(12) United States Patent
Wilson et al.

(10) Patent No.: US 11,708,283 B2
(45) Date of Patent: Jul. 25, 2023

(54) METAL-CHELATING COMPOSITIONS AND THEIR USE IN METHODS OF REMOVING OR INHIBITING BARIUM SCALE

(71) Applicant: CORNELL UNIVERSITY, Ithaca, NY (US)

(72) Inventors: Justin Wilson, Ithaca, NY (US); Nikki Thiele, Brooktondale, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/734,061

(22) PCT Filed: May 31, 2019

(86) PCT No.: PCT/US2019/034794
§ 371 (c)(1),
(2) Date: Dec. 1, 2020

(87) PCT Pub. No.: WO2019/232294
PCT Pub. Date: Dec. 5, 2019

(65) Prior Publication Data
US 2021/0221715 A1    Jul. 22, 2021

Related U.S. Application Data

(60) Provisional application No. 62/679,138, filed on Jun. 1, 2018.

(51) Int. Cl.
*C02F 1/68* (2006.01)
*C02F 5/12* (2006.01)
(Continued)

(52) U.S. Cl.
CPC ............... *C02F 1/683* (2013.01); *C02F 5/12* (2013.01); *C02F 5/14* (2013.01); *C07D 413/14* (2013.01);
(Continued)

(58) Field of Classification Search
None
See application file for complete search history.

(56) References Cited

U.S. PATENT DOCUMENTS

| | | | |
|---|---|---|---|
| 4,190,462 A | 2/1980 | De Jong et al. | |
| 4,597,903 A * | 7/1986 | Gokel | C07D 407/14 540/467 |

(Continued)

FOREIGN PATENT DOCUMENTS

| | | | | |
|---|---|---|---|---|
| WO | WO-2016116555 A1 * | 7/2016 | ........... | C07C 253/30 |
| WO | 2017/103545 A1 | 6/2017 | | |
| WO | WO-2017103545 A1 * | 6/2017 | ............. | B01D 9/005 |

OTHER PUBLICATIONS

Zhang et al. (J. Am. Chem. Soc., 1995, 117, 11507-11511). (Year: 1995).*

(Continued)

*Primary Examiner* — Clare M Perrin
(74) *Attorney, Agent, or Firm* — Foley & Lardner LLP

(57) ABSTRACT

Metal-chelating compositions having the structure (1a) wherein: $R^1$, $R^2$, $R^3$, and $R^4$ are independently selected from the following groups: (i) hydrogen atom, (ii) hydrocarbon groups (R) containing 1-12 carbon atoms; (iii) halogen atoms; (iv) —P($R^5$)(=O)OH groups; (v) —C(=O)OH groups; (vi) —S(=O)$_2$OH groups; and (vii) —OH groups, wherein $R^5$ is selected from hydrocarbon groups (R) and —OH; $R^1$ and $R^2$ may optionally interconnect to form Ring A fused to the ring on which $R^1$ and $R^2$ are present; $R^3$ and $R^4$ may optionally interconnect to form Ring B fused to the ring on which $R^3$ and $R^4$ are present; wherein Ring A and Ring B are optionally and independently substituted with one or more of groups (ii)-(vii). Methods of using the above-described compositions for chelating metal ions having an atomic number of at least 56 (e.g., Ba or Ra) are also described.

(Continued)

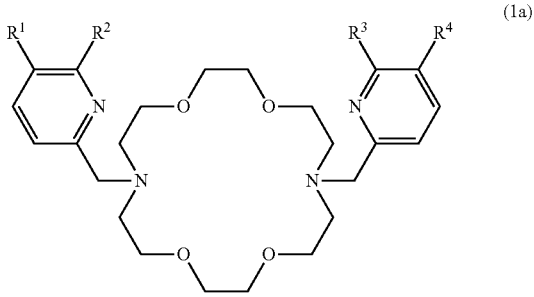

(1a)

19 Claims, 8 Drawing Sheets

(51) Int. Cl.
  C02F 5/14 (2006.01)
  C07D 413/14 (2006.01)
  C07F 9/6533 (2006.01)
  C02F 101/00 (2006.01)
(52) U.S. Cl.
  CPC ...... *C07F 9/6533* (2013.01); *C02F 2101/006* (2013.01)

(56) References Cited

U.S. PATENT DOCUMENTS

| | | | | |
|---|---|---|---|---|
| 4,631,119 | A * | 12/1986 | Gokel | C07D 323/00 205/423 |
| 4,687,844 | A * | 8/1987 | Gokel | C07D 273/00 540/467 |
| 5,747,345 | A * | 5/1998 | Weber, II | G01N 33/84 534/751 |
| 2018/0362550 | A1* | 12/2018 | Maury | C07D 413/14 |

OTHER PUBLICATIONS

Roca-Sabio et al. (J. Am. Chem. Soc., 2009, 131, 3331-3341. (Year: 2009).*
Roca-Sabio et al. (Dalton Trans., 2011, 40, 384-392). (Year: 2011).*
Almubarak, T., et al., "Oilfield Scale Removal by Chelating Agents: An Aminopolycarboxylic Acids Review", SPE-185636-MS, Society of Petroleum Engineers, 2017, pp. 1-13.
Ferreiros-Martinez, R., et al., "Macrocyclic Receptor Showing Extremely High Sr(II)/Ca(II) and Pb(II)/Ca(II) Selectivities with Potential Application in Chelation Treatment of Metal Intoxication", Inorganic Chemistry 2011, Published Mar. 17, 2011, pp. 3772-3784, 50.
International Search Report dated Aug. 28, 2019 issued in PCT/US 19/34794, 1 page.
Mato-Iglesias, M., et al., "Lanthanide Complexes Based on a 1,7-Diaza-12-crown-4 Platform Containing Picolinate Pendants: A New Structural Entry for the Design of Magnetic Resonance Imaging Contrast Agents", Inorganic Chemistry 2008, Published on web Aug. 2, 2008, pp. 7840-7851, vol. 47, No. 17.
National Center for Biotechnology Information, "2,2'-[1,4,10,13-Tetraoxa-7,16-diazacyclooctadecane-7,16-diylbis(methylene)]bis(quinoline-8-ol)", PubChem Compound Summary for CID 10531251, https://pubchem.ncbi.nlm.nih.gov/compound/10531251, Created Oct. 25, 2006, 7 pages.
Roca-Sabio, A., et al., "Macrocyclic Receptor Exhibiting Unprecedented Selectivity for Light Lanthanides", J. Am. Chem. Soc. 2009, Published on Web Feb. 18, 2009, pp. 3331-3341, vol. 131, No. 9.
Thiele, N.A., et al., "An Eighteen-Membered Macrocyclic Ligand for Actinium-225 Targeted Alpha Therapy", Angew. Chem. Int. Ed. 2017, Manuscript, Accepted manuscript online Sep. 29, 2017, Version of record online: Oct. 16, 2017, pp. 14712-14717, 56.
Thomae, A.V., et al., "Permeation of Aromatic Carboxylic Acids across Lipid Bilayers: The pH-Partition Hypothesis Revisited", Biophysical Journal, Sep. 2005, pp. 1802-1811, vol. 89.
Zhang, X.X., et al., "A New Highly Selective Macrocycle for K+ and Ba2+: Effect of Formation of a Pseudo Second Macroring through Complexation", J. Am. Chem. Soc. 1995, pp. 11507-11511, 117.
Alberty et al., "Recommendations for nomenclature and tables in biochemical thermodynamics", Eur. J. Biochem., vol. 240, 1996, pp. 1-14.
Baes et al., "The Hydrolysis of Cations", Wiley: New York, 1976.
Boros et al., "Acyclic Chelate with Ideal Properties for 68Ga PET Imaging Agent Elaboration—Supp Data", J Am. Chem. Soc., vol. 132, 2010, pp. 15726-15733.
Clarke et al., "Stabilities of the alkaline earth and divalent transition metal complexes of the tetraazamacrocyclic tetraacetic acid ligands", Inorganica Chimica Acta, vol. 190, 1991, pp. 27-36.
Clemmit et al., "The Dissolution of Scales in Oilfield Systems", SPE14010/1, presented at SPE, Aberdeen, U.K. Sep. 10-13, 1985.
Greenwood et al., "Chemistry of the Elements", Butterworth Heinemann, 1997, pp. 107-138.
Harris et al., "Coordination chemistry of microbial iron transport compounds. 16. Isolation, characterization, and formation constants of ferric aerobactin", J. Am. Chem. Soc., vol. 101, 1979, pp. 2722-2727.
Li et al., "Scale formation and control in oil and gas fields: A review", J. Dispersion Sci. Tech., vol. 38, 2017, pp. 661-670.
Lide et al., "Handbook of Chemistry and Physics", CRC Press: Boca Raton, 2006.
Martell et al., "Critical Stability Constants, vol. I: Amino Acids"; Plenum Press: New- York; London, 1974.
N. Su et al., "Syntheses and Metal Ion Complexation—Supp Data", J. Org. Chem., 64, 1999, pp. 8855-8861.
Schmitt-Willich et al., "Synthesis and Physicochemical Characterization of a New Gadolinium Chelate: The Liver-Specific Magnetic Resonance Imaging Contrast Agent Gd-EOB-DTPA", Inorg. Chem., vol. 38, 1999, pp. 1134-1144.
Sheldrick et al., "A short history of SHELX", Acta Crystallogr. Sect. A, vol. 64, 2008, pp. 112-122.
Zielinski et al., "Naturally Occurring Radioactive Materials (NORM) in Produced Water and Oil-Field Equipment—An Issue for the Energy Industry", U.S. Geological Survey Fact Sheet FS-142-99, Sep. 1999.

* cited by examiner

METAL-CHELATING COMPOSITIONS AND THEIR USE IN METHODS OF REMOVING OR INHIBITING BARIUM SCALE

CROSS-REFERENCE TO RELATED APPLICATIONS

This application claims priority from U.S. Provisional Application No. 62/679,138, filed Jun. 1, 2018, which is herein incorporated by reference in its entirety.

STATEMENT REGARDING FEDERALLY SPONSORED RESEARCH

This invention was made with government support under a Pilot Award from the Weill Cornell Medical College Clinical and Translational Science Center under grant number UL1TR00457 awarded by the National Institutes of Health (NIH) and National Center for Advancing Translational Services (NCATS). The government has certain rights in the invention.

BACKGROUND OF THE DISCLOSURE

Barium, the 14th most abundant element in the Earth's crust, is the heaviest and largest non-radioactive alkaline earth (AE) metal (Chemistry of the Elements, 2nd Ed.; Greenwood, N., Earnshaw, A., Eds.; Butterworth-Heinemann: Oxford, 1997; pp 107-138). Administered as a suspension of $BaSO_4$, this element has been employed for over a century as a contrast agent for X-ray imaging of the gastrointestinal tract. The insolubility of $BaSO_4$ ($K_{sp}=1.08\times 10^{-10}$) is essential for its use in medicine because it prevents this toxic heavy metal from being absorbed into the body (CRC Handbook of Chemistry and Physics, 87th ed.; Lide, D. R., Ed.; CRC Press: Boca Raton, 2006). This same physical property, however, presents a serious problem in the industrial sector. Precipitation of $BaSO_4$ occurs frequently in oil field and gas production operations. When barium-rich waters mix with sulfate-rich seawater, an intractable scale of $BaSO_4$ is deposited, obstructing downhole pipes and surface equipment (Li, J.; Tang, M.; Ye, Z.; Chen, L.; Zhou, Y., J. Dispersion Sci. Technol. 2017, 38, 661-670). As such, $BaSO_4$ scale is a major economic burden to the petroleum industry that slows or halts production and requires costly scale removal (Clemmit, A. F.; Ballance, D. C.; Hunton, A. G. The dissolution of scales in oilfield systems. SPE14010/1, presented at SPE, Aberdeen, U.K. Sep. 10-13, 1985). In addition, the scale poses a significant health hazard to petroleum workers. Naturally occurring radioactive material (NORM), particularly long-lived bone-seeking $Ra^{2+}$ ions, is readily incorporated into $BaSO_4$ and is mobilized during scale remediation, exposing humans to toxic levels of radioactivity (Zielinski, R. A; Otton, J. K., U.S. Geological Survey Fact Sheet FS-142-99, September, 1999). Hence, the efficient and safe removal of $BaSO_4$ scale is of global significance.

The elimination of $BaSO_4$ scale is conventionally achieved by solubilization using chelating agents. One of the most commonly used chelators is the acyclic ligand diethylenetriamine pentaacetic acid (i.e., DTPA, with structure shown in FIG. 1). The thermodynamic stabilities of DTPA complexes of the AEs, however, decrease with increasing ionic radius of the metal ion, rendering DTPA a low-affinity ligand for $Ba^{2+}$ (log $K_{BaL}=8.78$) (Martell, A. E.; Smith, R. M. Critical Stability Constants: Vol. 1; Plenum Press: New York; London, 1974). Extreme conditions of high pH (pH>11) and heat are required to efficiently remove scale using DTPA, reflecting the fact that this ligand is not optimal for the chelation of $Ba^{2+}$ (Dunn, K.; Yen, T. F. Environ. Sci. Technol. 1999, 33, 2821-2824; Putnis, C. V.; Kowacz, M.; Putnis, A. Appl. Geochem. 2008, 23, 2778-2788). The tetraaza macrocycle DOTA (FIG. 1) is also well known for its use in the dissolution of $BaSO_4$. Despite having the highest reported thermodynamic affinity for $Ba^{2+}$ in aqueous solution (log $K_{BaL}=11.75$), DOTA dissolves $BaSO_4$ less efficiently than DTPA, reflecting the slow metal-binding kinetics of this macrocycle (Clarke, E. T.; Martell, A. E. Inorg. Chim. Acta 1991, 190, 27-36).

Efforts in finding more effective $Ba^{2+}$ chelators for the removal of $BaSO_4$ scale have been largely unsuccessful. A key challenge for the chelation of $Ba^{2+}$ arises from the fact that large AEs engage primarily in ionic, rather than covalent, binding interactions with ligands. The strength of these ionic bonds is proportional to the charge-to-size ratio of the metal center, with smaller ratios giving rise to weaker electrostatic interactions. As the largest non-radioactive +2 ion in the Periodic Table (IR=1.35 Å, CN6), $Ba^{2+}$ has a low charge density, which results in coordination complexes of lower stability compared to the smaller AEs. As a result, the selective, rapid, and stable chelation of $Ba^{2+}$ has remained elusive.

BRIEF SUMMARY OF THE DISCLOSURE

In one aspect, the present disclosure is directed to a metal-chelating composition that has an exceptional ability for chelating the heavier elements, particularly those elements having an atomic number of at least 56, such as barium and radium. More particularly, the metal-chelating composition has the following structure:

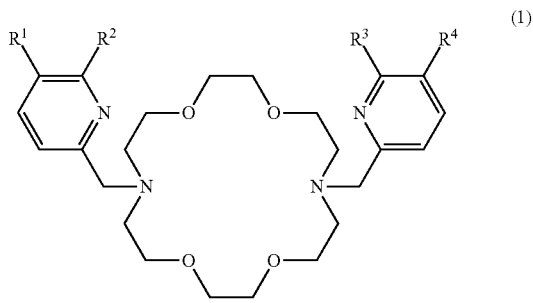

(1)

wherein: $R^1$, $R^2$, $R^3$, and $R^4$ are independently selected from the following groups: (i) hydrogen atom, (ii) hydrocarbon groups (R) containing 1-12 carbon atoms; (iii) halogen atoms; (iv) —P($R^5$)(=O)OH groups; (v) —C(=O)OH groups; (vi) —S(=O)$_2$OH groups; and (vii) —OH groups, wherein $R^5$ is selected from hydrocarbon groups (R) and —OH; $R^1$ and $R^2$ may optionally interconnect to form Ring A fused to the ring on which $R^1$ and $R^2$ are present; $R^3$ and $R^4$ may optionally interconnect to form Ring B fused to the ring on which $R^3$ and $R^4$ are present; wherein Ring A and Ring B are optionally and independently substituted with one or more of groups (ii)-(vii). In some embodiments, at least one of $R^2$ and $R^3$ is selected from groups (iv)-(vii) or groups (iv)-(vi), or at least one of Ring A and Ring B is present and is substituted with at least one group selected from groups (iv)-(vii) or groups (iv)-(vi).

In another aspect, the present disclosure is directed to methods for chelating a heavy metal ion having an atomic number of at least 56, the method comprising contacting a salt of the metal ion with the above-described metal-chelating composition while both the salt and metal-chelating composition are in contact with an aqueous-based liquid. In a first set of particular embodiments, the metal ion is within a barium scale deposit, and the method results in dissolution of the barium and/or other heavy metal ion from the barium scale deposit into the aqueous-based liquid to result in at least partial removal of the barium scale deposit. In a second set of particular embodiments, a barium-containing aqueous liquid is in contact with a processing component (e.g., a conduit for transporting and/or processing of the barium-containing aqueous liquid), and the metal-chelating composition is dissolved in the barium-containing aqueous liquid to inhibit formation or growth of a barium scale deposit on the processing component.

BRIEF DESCRIPTION OF THE FIGURES

FIG. 5A shows the results of dissolution of $BaSO_4$ at room temperature (RT) and pH 8, as initiated by the addition of chelator (5 mM) to a suspension of $BaSO_4$ (4.53 mM Ba($NO_3$)$_2$ and 13.48 mM $Na_2SO_4$). Barium content in solution was measured by GFAAS after 10, 20, and 30 min. FIG. 5B are photos of samples from dissolution experiments of $BaSO_4$ after 30 minutes for various chelating ligands (macropa, macropaquin, DTPA, DOTA, and no ligand).

FIG. 6A is an image of large rocks of crude barite ore were crushed with a hammer. FIG. 6B is an image showing barite sieved to isolate particles between 0.5 and 2 mm. FIG. 6C is an image showing simulation of petroleum pipes clogged with $BaSO_4$ scale. For the simulation, columns were filled with barite (3 g), and then solutions of macropa or DTPA (~48 mM) at pH 8 and pH 11 were added. FIG. 6D shows the ligand efficiency, or the percent of ligand saturated with $Ba^{2+}$, as determined by measuring the concentration of barium in the eluate by GFAAS after a soak period of 1 hour.

DETAILED DESCRIPTION OF THE DISCLOSURE

Figure 1:
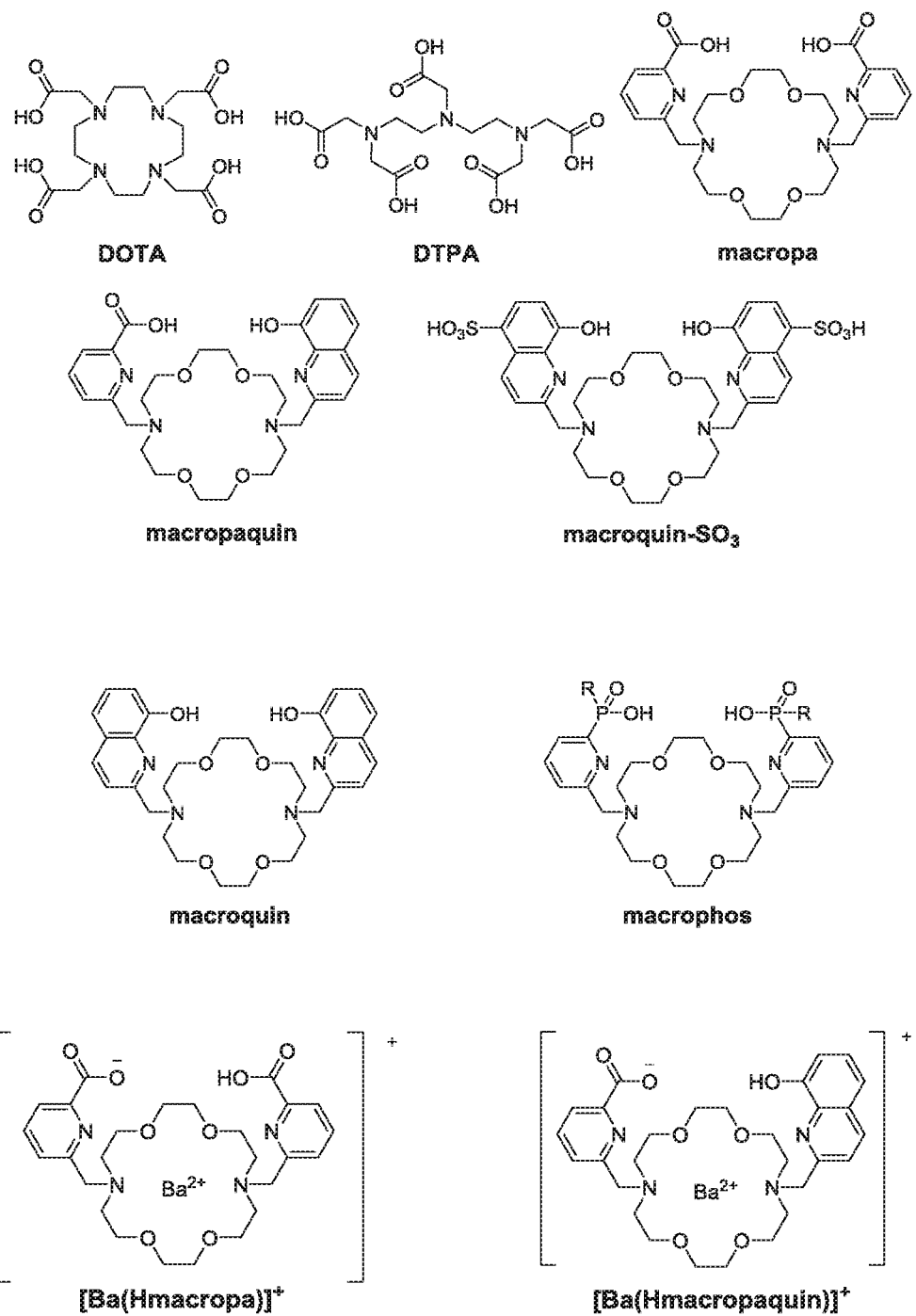
FIG. 1 shows the structures of some exemplary metal-chelating agents and complexes with barium.

As used herein, the term "hydrocarbon group" (also denoted by the group R) is, in a first embodiment, composed solely of carbon and hydrogen. The hydrocarbon group may contain, for example, one, two, three, four, five, six, seven, eight, nine, ten, eleven, or twelve carbon atoms, or a number of carbon atoms within a range therein (e.g., 1-12, 2-12, or 3-12 carbon atoms). The hydrocarbon group composed solely of carbon and hydrogen can be, for example, an alkyl, alkenyl, cycloalkyl, cycloalkenyl (aliphatic), or aromatic group.

Some examples of straight-chained (linear) alkyl groups include methyl, ethyl, n-propyl, n-butyl, n-pentyl, n-hexyl, n-heptyl, n-octyl, n-nonyl, n-decyl, n-undecyl, and n-dodecyl groups. Some examples of branched alkyl groups include isopropyl (2-propyl), isobutyl (2-methylprop-1-yl), sec-butyl (2-butyl), t-butyl, 2-pentyl, 3-pentyl, 2-methylbut-1-yl, isopentyl (3-methylbut-1-yl), 1,2-dimethylprop-1-yl, 1,1-dimethylprop-1-yl, neopentyl (12-dimethylprop-1-yl), 2-hexyl, 3-hexyl, 2-methylpent-1-yl, 3-methylpent-1-yl, and isohexyl (4-methylpent-1-yl), wherein the "1-yl" suffix represents the point of attachment of the group.

Some examples of straight-chained olefinic (alkenyl) groups include vinyl, propen-1-yl (allyl), 3-buten-1-yl ($CH_2$=CH—$CH_2$—$CH_2$—), 2-buten-1-yl ($CH_2$=CH=CH—$CH_2$—), butadienyl, and 4-penten-1-yl groups. Some examples of branched olefinic groups include propen-2-yl, 3-buten-2-yl (CH=CH—CH.—$CH_3$), 3-buten-3-yl ($CH_2$=C.—$CH_2$—$CH_3$), 4-penten-2-yl, 4-penten-3-yl, 3-penten-2-yl, 3-penten-3-yl, and 2,4-pentadien-3-yl, wherein the dot in the foregoing exemplary formulas represents a radical (i.e., the point of attachment of the group).

Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane).

Some examples of cycloalkenyl (aliphatic) groups include cyclopropenyl, cyclobutenyl, cyclopentenyl, cyclopentadienyl, cyclohexenyl, cyclohexadienyl, cycloheptenyl, cycloheptadienyl, cyclooctenyl, cyclooctadienyl, and cyclooctatetraenyl groups. Some examples of aromatic groups include phenyl and benzyl. The aromatic hydrocarbon group can also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene.

In another embodiment, the term "hydrocarbon group" (R) contains at least one heteroatom (i.e., non-carbon and non-hydrogen atom), such as one or more heteroatoms selected from oxygen, nitrogen, sulfur, and halide atoms, or groups containing one or more of these heteroatoms (i.e., heteroatom-containing groups). One or more of the heteroatoms (e.g., oxygen, nitrogen, and/or sulfur atoms) can be inserted between carbon atoms (e.g., as —O—, —NR'—, or —S—) in any of the hydrocarbon groups described above. Alternatively, or in addition, one or more of the heteroatom-containing groups can replace one or more hydrogen atoms on the hydrocarbon group. In some embodiments, the hydrocarbon group contains at least one halogen atom (such as in —$CF_3$).

Some examples of oxygen-containing groups include hydroxy (OH), alkoxy (OR), carbonyl-containing (e.g., carboxylic acid, ketone, aldehyde, carboxylic ester, amide, and urea functionalities), nitro (NO₂), carbon-oxygen-carbon (ether), sulfonyl, and sulfinyl (i.e., sulfoxide) groups. Some particular examples of alkoxy groups (—OR) include methoxy, ethoxy, n-propoxy, isopropoxy, n-butoxy, isobutoxy, t-butoxy, phenoxy, benzyloxy, 2-hydroxyethoxy, 2-methoxyethoxy, 2-ethoxyethoxy, vinyloxy, and allyloxy groups. In the case of an ether group, the ether group can also be a polyalkyleneoxide (polyalkyleneglycol) group, such as a polyethyleneoxide group. Some examples of nitrogen-containing groups include primary amine, secondary amine, tertiary amine (i.e., —NR'₂, wherein R' is independently selected from H and hydrocarbon groups set forth above), nitrile (CN), amide (i.e., —C(O)NR₂ or —NRC(O)R', wherein R' is independently selected from hydrogen atom and hydrocarbon groups set forth above), imine (e.g., —CR'=NR', wherein R' is independently H or a hydrocarbon group), urea (—NR'—C(O)—NR'₂, wherein R is independently H or a hydrocarbon group), and carbamate groups (—NR'—C(O)—OR', wherein R' is independently H or a hydrocarbon group). Some examples of sulfur-containing groups include mercapto (i.e., —SH), thioether (i.e., sulfide, e.g., —SR), disulfide (—R—S—S—R), sulfoxide (—S(O)R), sulfone (—SO₂R), sulfonate (—S(=O)₂OR", wherein R" is H, a hydrocarbon group, or a cationic group), and sulfate groups (—OS(=O)₂OR", wherein R" is H, a hydrocarbon group, or a cationic group). Some examples of halide atoms include fluorine, chlorine, bromine, and iodine.

In a first aspect, the present disclosure is directed to a metal-chelating composition (i.e., molecule or ligand) having the following structure:

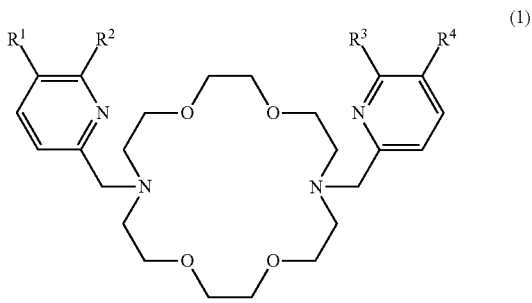
(1)

In Formula (1), $R^1$, $R^2$, $R^3$, and $R^4$ are independently selected from the following groups: (i) hydrogen atom, (ii) hydrocarbon groups (R) containing 1-12 carbon atoms; (iii) halogen atoms (e.g., F, Cl, Br, or I); (iv) —P($R^3$)(=O)OH groups; (v) —C(=O)OH groups; (vi) —S(=O)₂OH groups (sulfonic acid or sulfonate group); and (vii) —OH groups, wherein $R^7$ is selected from hydrocarbon groups (R) and —OH. When $R^5$ is OH, group (iv) is —P(=O)(OH)₂, i.e., a phosphonic acid (phosphonate) group. When $R^5$ is OH, group (iv) is a phosphinic acid (phosphinate) group. In Formula (1), at least one (or precisely one) of $R^2$ and $R^3$ is selected from groups (iv)-(vii) or at least one (or precisely one) of $R^2$ and $R^3$ is selected from groups (iv)-(vi). In some embodiments, $R^2$ and $R^3$ are not both group (iv) or are not both group (v) or are not both group (vi) or are not both group (vii). $R^2$ and $R^3$ may be the same or different. In some embodiments, $R^1$ and $R^4$ are independently selected from groups (i), (ii), and/or (iii).

$R^1$ and $R^2$ may optionally interconnect to form Ring A fused to the ring on which $R^1$ and $R^2$ are present. Ring A is typically a fused benzene ring, but other fused rings are possible. When Ring A is present, the structure according to Formula (1) can be represented as follows, the case where Ring A is selected as a benzene ring:

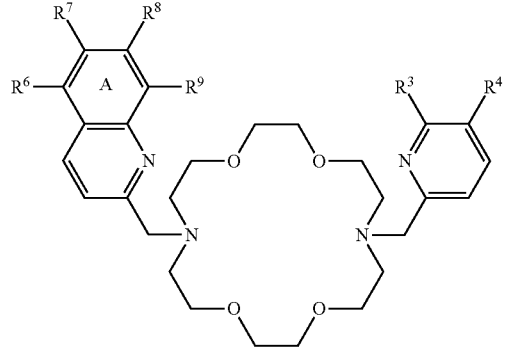
(1a)

In Formula (1a) above, Ring A is represented by "A", and $R^6$, $R^7$, $R^8$, and $R^9$ on Ring A are independently selected from groups (i), (ii), (iii), (iv), (v), (vi), and (vii) as defined above under Formula (1). Thus, Ring A is optionally substituted with one or more groups (ii)-(vii). $R^1$ and $R^4$ are as defined above under Formula (1) and may be selected from all of the groups recited above independent of selections made for $R^6$, $R^7$, $R^8$, and $R^9$. In Formula (1a), at least one (or precisely one) of $R^6$, $R^7$, $R^8$, and $R^9$ is selected from groups (iv)-(vii) or at least one (or precisely one) of $R^6$, $R^7$, $R^8$, and $R^9$ is selected from groups (iv)-(vi). In particular embodiments of Formula (1a), $R^9$ is selected from groups (iv)-(vii) or $R^9$ is selected from groups (iv)-(vi), or $R^9$ may be (iv), (v), (vi), or (vii). In some embodiments, $R^6$, $R^7$, and $R^8$ are independently selected from groups (i), (ii), and/or (iii). In some embodiments, $R^3$ and $R^9$ are independently selected from groups (iv)-(vii) or groups (iv)-(vi). $R^3$ and $R^9$ may be the same or different. In some embodiments, $R^4$, $R^6$, $R^7$, and $R^8$ are independently selected from groups (i), (ii), and/or (iii).

In other embodiments of Formula (1), $R^3$ and $R^4$ may optionally interconnect to form Ring B fused to the ring on which $R^3$ and $R^4$ are present. When Ring B is present, the structure according to Formula (1) can be represented as follows, where Ring B is selected as a benzene ring:

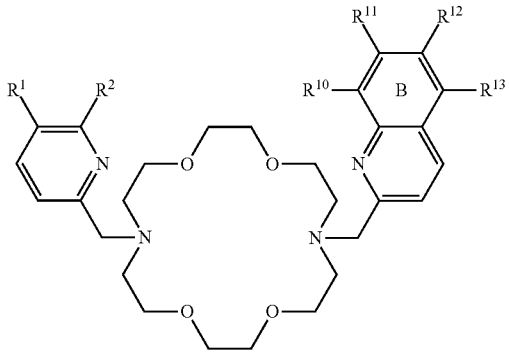
(1b)

In Formula (1b) above, Ring B is represented by "B", and $R^{10}$, $R^{11}$, $R^{12}$, and $R^{13}$ on Ring B are independently selected from groups (i), (ii), (iii), (iv), (v), (vi), and (vii) as defined above under Formula (1). Thus, Ring B is optionally substituted with one or more groups (ii)-(vii). $R^1$ and $R^2$ are as defined above under Formula (1) and may be selected from all groups recited above independent of selections made for $R^{10}$, $R^{11}$, $R^{12}$ and $R^{13}$. In Formula (1b), at least one (or precisely one) of $R^{10}$, $R^{11}$, $R^{12}$, and $R^{13}$ is selected from groups (iv)-(vii) or at least one (or precisely one) of $R^{10}$, $R^{11}$, $R^{12}$, and $R^{13}$ is selected from groups (iv)-(vi). In particular embodiments of Formula (1b), $R^{10}$ is selected from groups (iv)-(vii) or $R^{10}$ is selected from groups (iv)-(vi), or $R^{10}$ may be (iv), (v), (vi), or (vii). In some embodiments, $R^{11}$, $R^{12}$, and $R^{13}$ are independently selected from groups (i), (ii), and/or (iii). In some embodiments, $R^2$ and $R^{10}$ are independently selected from groups (iv)-(vii) or groups (iv)-(vi). $R^2$ and $R^{10}$ may be the same or different. In some embodiments, $R^1$, $R^{11}$, $R^{12}$, and $R^{13}$ are independently selected from groups (i), (ii), and/or (iii).

In other embodiments of Formula (1), $R^1$ and $R^2$ interconnect to form Ring A, and $R^3$ and $R^4$ interconnect to form Ring B. When both Ring A and Ring B are present, the structure according to Formula (1) can be represented as follows, where Ring A and Ring B are both selected as benzene rings:

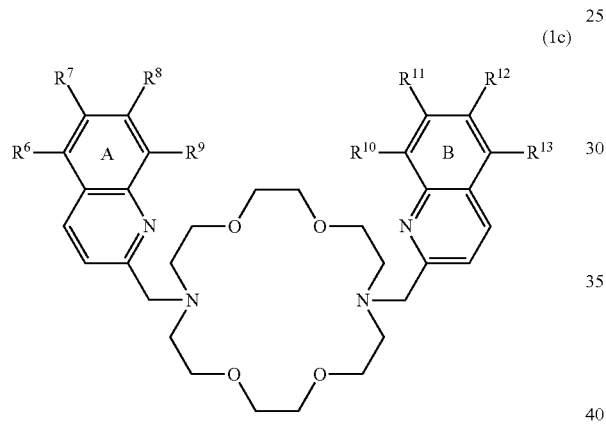

(1c)

In Formula (1c), $R^6$, $R^7$, $R^8$, $R^9$, $R^{10}$, $R^{11}$, $R^{12}$, and $R^{13}$ are independently selected from groups (i), (ii), (iii), (iv), (v), (vi), and (vii) as defined above under Formula (1). Thus, Ring A is optionally substituted with one or more groups (ii)-(vii) and Ring B is optionally substituted with one or more groups (ii)-(vii), provided that at least one of Ring A and Ring B is substituted with at least one group selected from groups (iv)-(vi) or at least one group selected from groups (iv)-(vii), or at least one of Ring A and Ring B is substituted with at least one of (iv), (v), (vi), or (vii). Thus, the possibility exists for one of Ring A or Ring B being substituted with only group (ii) or (iii), but this condition is accompanied by the other Ring A or Ring B being substituted with one or more of groups (iv), (v), (vi), and (vii). Stated differently, at least one (e.g., one, two, three, or four) of $R^6$, $R^7$, $R^8$, $R^9$, $R^{10}$, $R^{11}$, $R^{12}$, and $R^{13}$ is selected from groups (iv), (v), (vi), and (vii) or subset thereof. In particular embodiments of Formula (1c), at least one of $R^9$ and $R^{10}$ is selected from groups (iv)-(vii) or from groups (iv)-(vi), or both $R^9$ and $R^{10}$ are selected from groups (iv)-(vii) or groups (iv)-(vi), or one or both of $R^9$ and $R^{10}$ may be group (iv), (v), (vi), or (vii). In some embodiments, $R^6$, $R^7$, $R^8$, $R^{11}$, $R^{12}$, and $R^{13}$ are independently selected from groups (i), (ii), and/or (iii).

In a first set of particular embodiments, at least one of $R^2$ and $R^3$ is group (v), i.e., —C(=O)OH, or at least one of Ring A and Ring B is present and is substituted with group (v). In some embodiments, both $R^2$ and $R^3$ in Formula (1) are group (v) or both $R^9$ and $R^{10}$ in Formula (1c) are group (v). The foregoing embodiments are exemplified by the following structures:

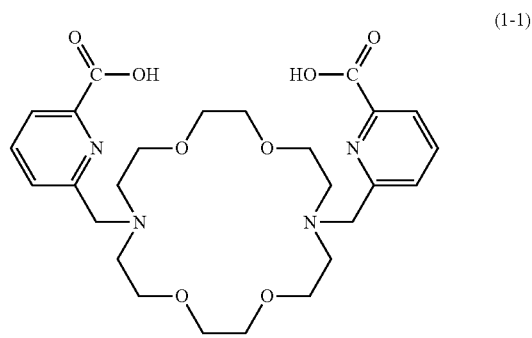

(1-1)

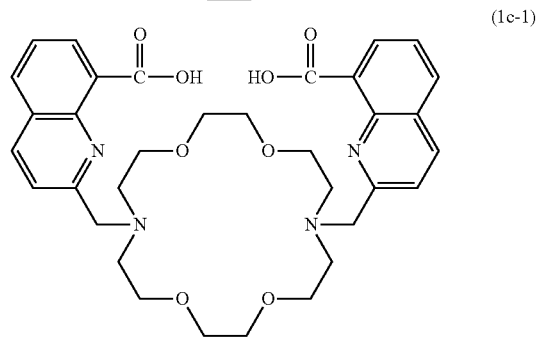

(1c-1)

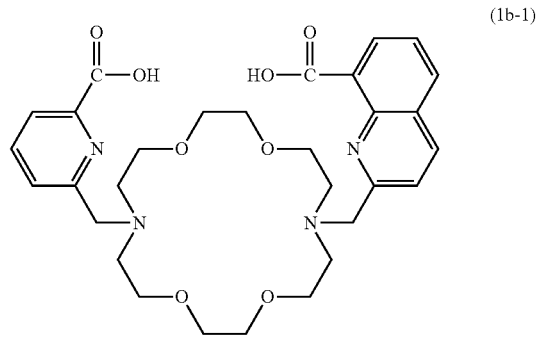 [SMILES: O=C(O)c1cccc2ccc(CN3CCOCCOCCN(Cc4cccc(O)n4)CCOCCOCC3)nc12]

(1b-1)

In a second set of particular embodiments, $R^2$ is group (v), i.e., —C(=O)OH, and either: $R^3$ is group (vii), i.e., —OH, or Ring B is present and is substituted with group (vii). The foregoing embodiments are exemplified by the following structures:

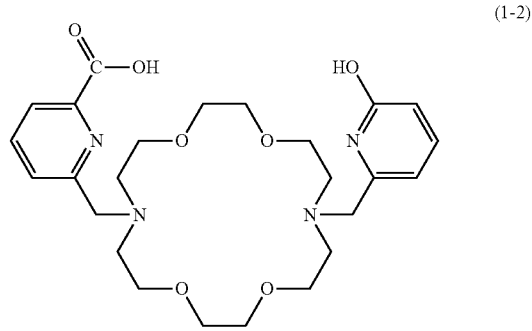

(1-2)

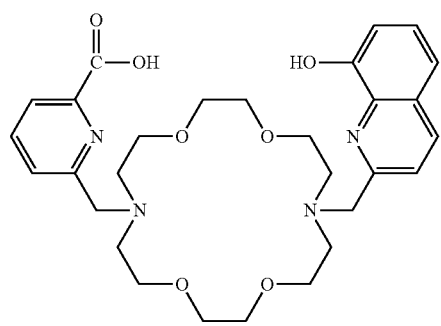
(1b-2)

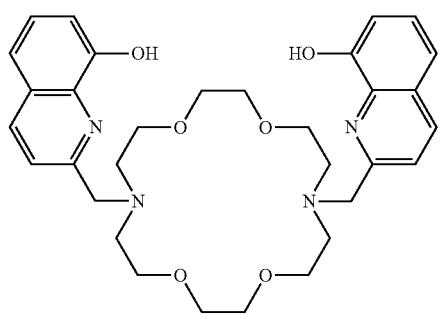
(1c-2)

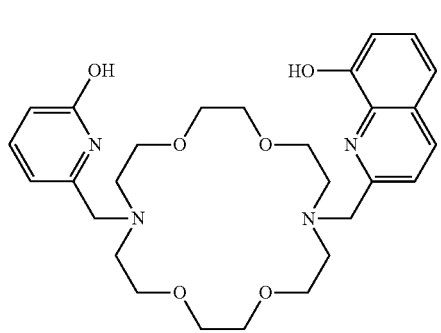
(1b-4)

In a third particular set of embodiments, R² is group (vii), i.e., —OH—, and Ring B is present and is substituted with group (v), i.e., —C(O)OH, such as exemplified by the following structure:

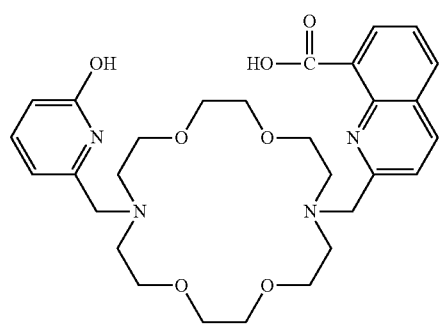
(1b-3)

In a fifth particular set of embodiments, at least one of R² and R³ is group (iv), i.e., —P(R³)(=O)OH, or at least one of Ring A and Ring B is present and is substituted with group (iv). In some embodiments, both R² and R³ in Formula (1) are group (iv) or both R⁹ and R¹⁰ in Formula (1c) are group (iv). The foregoing embodiments are exemplified by the following structures:

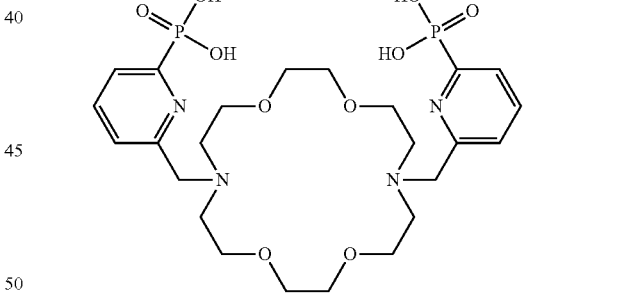
(1-4)

In a fourth particular set of embodiments, at least one of R² and R³ in Formula (1) is group (vii), i.e., —OH, or at least one of Ring A and Ring B is present and is substituted with at least one of group (vii). In some embodiments, both R² and R³ in Formula (1) are group (vii) or both R⁹ and R¹⁰ in Formula (1c) are group (vii). The foregoing embodiments are exemplified by the following structures:

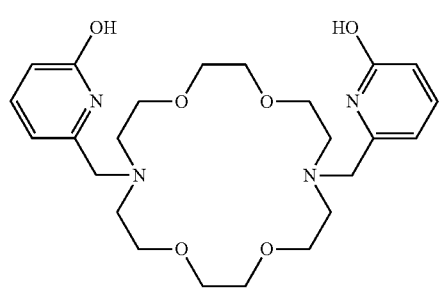
(1-3)

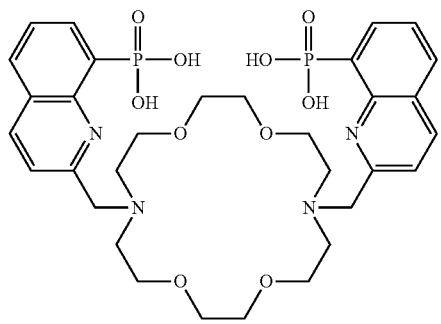
(1c-3)

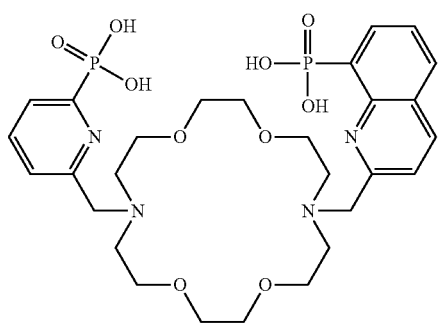
(1b-5)
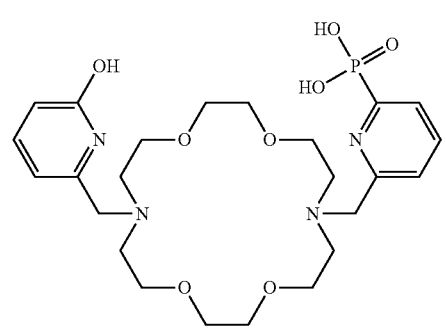
(1-5)
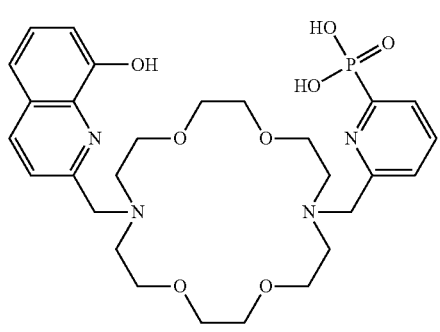
(1a-1)
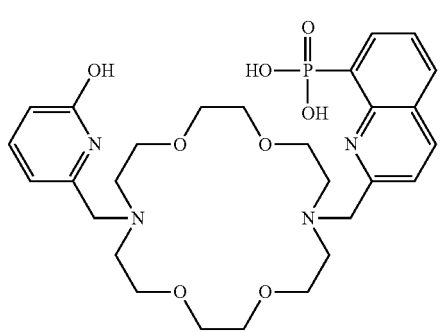
(1b-6)
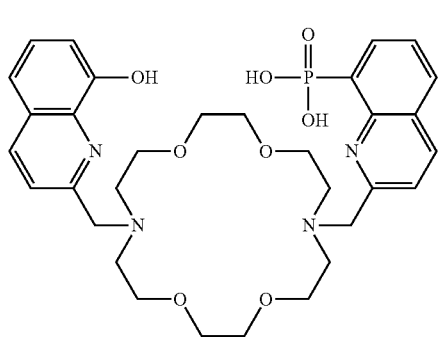
(1c-4)
In a sixth particular set of embodiments, at least one of $R^2$ and $R^3$ is group (vi), i.e., —S(=O)$_2$OH, or at least one of Ring A and Ring B is present and is substituted with group (vi). In some embodiments, both $R^2$ and $R^3$ in Formula (1) are group (vi) or both $R^9$ and $R^{10}$ in Formula (1e) are group (vi). The foregoing embodiments are exemplified by the following structures.
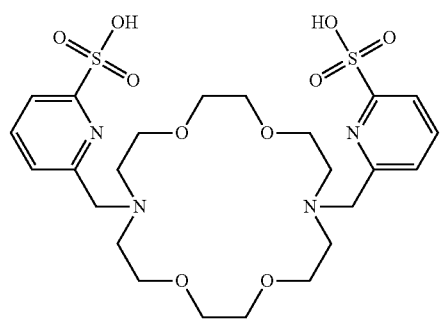
(1-5)
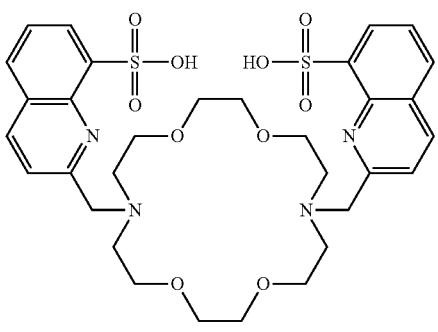
(1c-5)
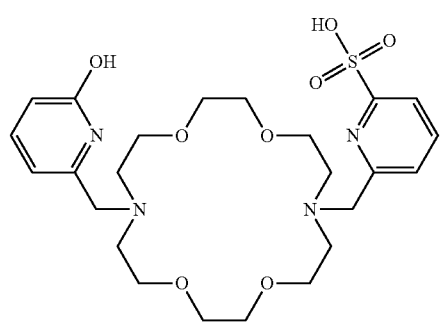
(1-6)
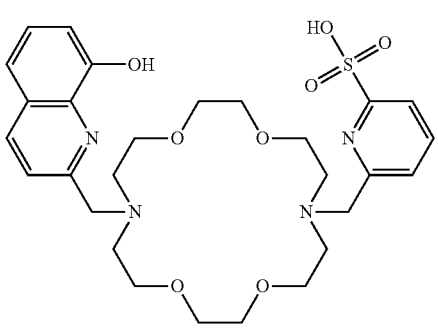
(1a-2)

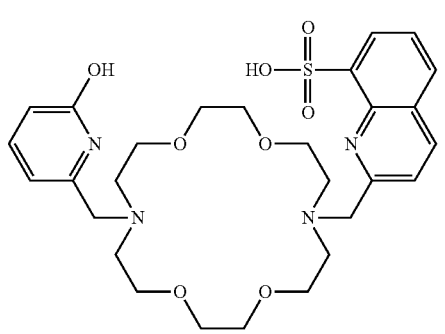

(1b-7)

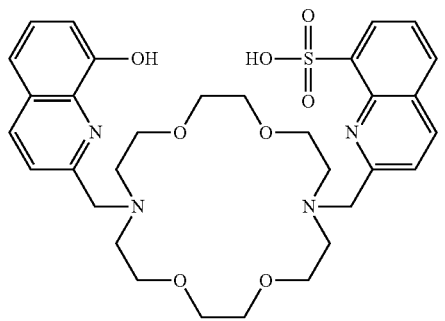

(1c-6)

Figure 2:
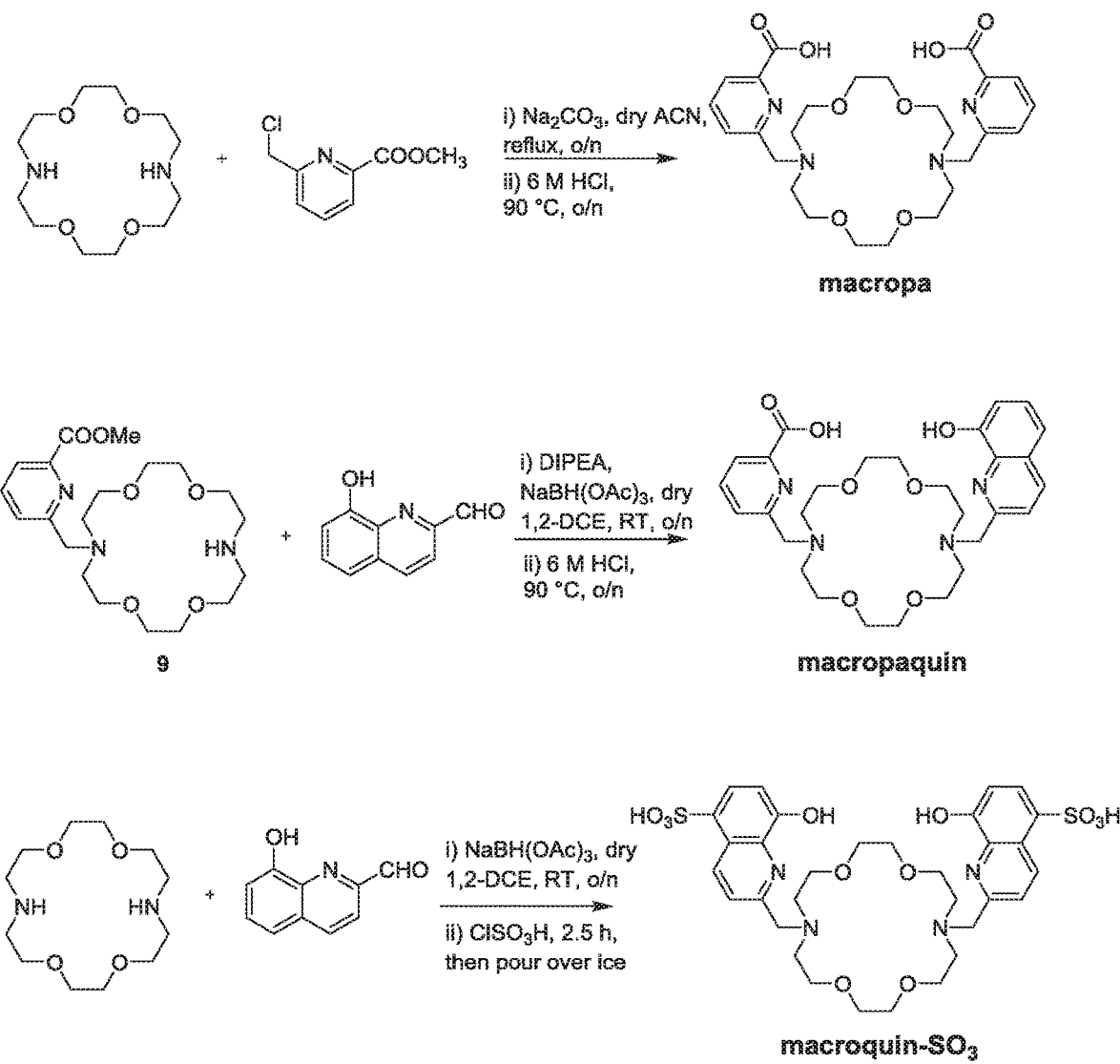
FIG. 2 shows a few possible reaction schemes for producing some exemplary metal-chelating agents (macropa, macropaquin, and macroquin-$SO_3$).

The metal-chelating molecules described above can be synthesized by methods well known in the art. For example, the structure of Formula (1-1), also referred to as "macropa" ((6,6-((1,4,10,13-tetraoxa-7,16-diazacyclooctadecane-7,16-diyl)bis(methylene))dipicolinic acid), can be prepared by synthetic methods described in, for example, A. Roca-Sabio et al., *J. Am. Chem. Soc.*, 131, 3331, 2009 and N. A. Thiele, *Angew Chem. Int. Ed.*, 56, 14712-14717, 2017, the contents of which are herein incorporated by reference. The foregoing methodology can be suitably modified to produce other metal-chelating structures described above. As an example, to produce the structure of Formula (1b-2), also referred to as "macropaquin" (6-((16-((8-hydroxyquinolin-2-yl)methyl)-1,4,10,13-tetraoxa-7,16-diazacyclooctadecan-7-yl)methyl)picolinic acid), methyl 6-((1,4,10,13-tetraoxa-7,16-diazacyclooctadecan-7-yl)methyl)picolinate can be reacted with 8-hydroxyquinoline-2-carbaldehyde in the presence of diisopropylethylanine (DIPEA) and NaBH(OAc)$_3$, followed by acid work-up and purification steps to produce the final product. FIG. 2 shows a few possible reaction schemes for producing some exemplary metal-chelating agents (macropa, macropaquin, and macroquin-SO$_3$).

In another aspect, the present disclosure is directed to methods for chelating metal ions having an atomic number of at least 56. The process of chelating such metal ions may be for the purpose of, for example, at least partially (or completely) removing a scale deposit containing one or more such metal ions, or the process may serve to at least partially inhibit or prevent the formation (or continued formation) of such a scale deposit. By proper selection of suitably hydrophobic or hydrophilic groups on the metal-chelating molecule, the chelation process may, in some embodiments, function to extract one or more such metal ions from a hydrophilic (e.g., aqueous) phase into another (generally more hydrophobic) liquid phase in which the metal-chelating molecule is soluble, wherein the liquid phases are insoluble with each other.

The metal ion having an atomic number of at least 56 may be, most notably, barium and/or radium. The metal ion may also (or alternatively) be selected from one or more of the lanthanides (e.g., any of the elements having atomic numbers of 57-71), such as lanthanum, cerium, praseodymium, neodymium, samarium, europium, gadolinium, terbium, dysprosium, holmium, erbium, thulium, ytterbium, and lutetium. The metal ion may also (or alternatively) be selected from one or more of the actinides (e.g., any of the elements having atomic numbers of 89-95), such as actinium, thorium, protactinium uranium, neptunium, and americium.

In the method, a metal salt (e.g., a sulfate or halide form) of the metal ion is contacted with any of the metal-chelating molecules described above while both the metal salt and metal-chelating molecules are in contact with an aqueous-based liquid. The term "in contact with" is intended to encompass situations in which the metal salt is dissolved in the aqueous solution or where the metal salt is not dissolved in solution (e.g., flocculated, precipitated, or as a scale deposit). In a situation where the metal salt is within a scale deposit (or otherwise flocculated or precipitated), for purposes of the invention, the undissolved metal salt needs to be in contact with the aqueous-based liquid since the aqueous-based liquid provides a medium for the metal-chelating molecules to make contact with the undissolved metal salt, to thereby chelate and remove metal ions from the undissolved metal salt. In the case of a scale deposit of a metal salt (e.g., barium scale deposit, which may or may not also contain radium), the metal-chelating molecules in the aqueous-based liquid bind to the barium ions and/or other metal ions (e.g., radium) having an atomic number above 56 within the scale deposit, to result in at least partial dissolution (i.e., at least partial removal) of the scale deposit. When the metal-chelating molecules chelate the metal ions having an atomic number of at least 56, the metal ions from the scale deposit are solubilized or dispersed into the aqueous-based liquid. In some embodiments, the metal-chelating molecule selectively chelates barium and/or radium over elements having an atomic number less than 56. In particular embodiments, the metal-chelating molecule selectively chelates barium and/or radium over lighter alkaline earth elements, such as magnesium, calcium, and/or strontium. A greater selectivity for a particular metal ion is typically reflected in a thermodynamic binding constant for the metal ion that is at least one order of magnitude larger than for another metal ion, such as a thermodynamic binding constant for barium and/or radium that is at least one order of magnitude larger than for the smaller alkaline earths.

The aqueous-based liquid is any liquid medium containing water, typically in a concentration of at least 20, 30, 40, 50, 60, 70, 80, or 90 vol % water. The aqueous-based liquid may or may not include a co-solvent that is water-soluble. Some examples of water-soluble co-solvents include alcohols (e.g., methanol, ethanol, propanol), acetone, nitrile solvents (e.g., acetonitrile, propionitrile, and butyronitrile), sulfoxide solvents (e.g., dimethyl sulfoxide, ethyl methyl sulfoxide, diethyl sulfoxide, methyl propyl sulfoxide, and ethyl propyl sulfoxide), and amide solvents (e.g., N,N-dimethylformamide and N,N-diethylformamide).

The metal salt scale can form on any equipment surface (typically constructed of metal) that comes in contact with the metal-containing liquid during processing of the metal-containing liquid. The metal salt scale most typically develops within conduits (e.g., pipes, tubes, troughs, or sluices) used for transporting and/or processing of an aqueous-containing liquid containing the metal salt, such as barium and/or radium salts. However, the metal salt scale can develop on processing equipment other than conduits, such as gratings, filtration devices, flow or mixing paddles, drilling equipment, and pump components. Thus, for the process to effectively remove scale, the portion of the equipment containing the scale should be within the aqueous-based liquid in which the metal-chelating composition is included. In some embodiments, the metal-chelating composition is dissolved in the metal-containing (e.g., barium-containing) aqueous-based liquid to inhibit the formation or growth of a metal scale deposit (e.g., barium scale deposit) on the equipment. In particular embodiments, the equipment does not contain metal salt scale and the metal-chelating composition is periodically or consistently maintained in the aqueous-based solution in contact with the equipment in order to prevent the formation of metal salt scale. In other embodiments, the equipment contains metal salt scale and the metal-chelating composition is periodically or consistently maintained in the aqueous-based solution in contact with the equipment in order to inhibit further growth of the scale or to reduce the rate of growth of the scale or to at least partially remove the scale.

Notably, by virtue of the exceptional chelating ability of the above described metal-chelating molecules, the above-described process for the dissolution of scale can be achieved under relatively mild conditions compared to conventional dissolution processes of the art. For example, the dissolution process described herein can typically be achieved at mild temperatures, such as a temperature of no more than 40, 35, 30, or 25° C. The dissolution process described herein can also typically be achieved at a pH of 5-10, or at a milder pH of, for example, 5-9, 5-8, 6-9, 6-8 or 6.5-7.5. The method described above can be practiced using any effective concentration of the metal chelating molecule in the aqueous-based solution in contact with the metal ions. The concentration of the chelating molecule may be precisely or at least, for example, 0.1 M, 0.2 M, 0.5 M, 1 M, 1.5 M, or 2 M, or a concentration within a range bounded by any two of the foregoing values.

The present disclosure also includes a process for metal-chelating molecule (ligand) recovery and reuse. In the process, a solution of the ligand-metal complex (e.g., macropa-dissolved $BaSO_4$) is acidified to release the metal (e.g., $Ba^{2+}$) from the ligand as the salt (e.g., $BaSO_4$). After filtration of the precipitated salt and basification of the solution, the recovered ligand can be reused for another cycle of metal salt dissolution.

Examples have been set forth below for the purpose of illustration and to describe the best mode of the invention at the present time. However, the scope of this invention is not to be in any way limited by the examples set forth herein.

EXAMPLES

Synthesis and Characterization of Ligands and Barium Complexes

Synthesis of macropa (6,6'-((1,4,10,13-tetraoxa-7,16-diazacyclooctadecane-7,16-diyl)bis(methylene)) dipicolinic acid)

The structure of macropa is shown in FIG. 1. An exemplary scheme for synthesizing macropa is provided in FIG. 2. The ligand was prepared according to literature procedures (Mato-Iglesias, et al., *Inorg. Chem.* 2008, 47, 7840-7851; and Roca-Sabio, A. et al., *J. Am. Chem. Soc.* 2009, 131, 3331-3341) and isolated as a $2HCl.4H_2O$ salt. Elemental analysis found: C, 46.27, 46.43; H, 6.75, 6.67; N, 8.25, 8.07. Calc. for $C_{26}H_{36}N_4O_8.2HCl.4H_2O$: C, 46.09; H, 6.84; N, 8.27.

Synthesis of macropaquin (6-((16-((8-hydroxyquinolin-2-yl)methyl)-1,4,10,13-tetraoxa-7,16-diazacyclooctadecan-7-yl)methyl)picolinic acid)

The structure of macropaquin is shown in FIG. 1. An exemplary scheme for synthesizing macropaquin is provided in FIG. 2. To a pale-yellow solution of methyl 6-((1,4,10,13-tetraoxa-7,16-diazacyclooctadecan-7-yl) methyl)picolinate.2TFA.1H$_2$O (0.6119 g, 0.93 mmol) in dry 1,2-dichloroethane (1,2-DCE) (23 mL) was sequentially added diisopropylethylamine (405 μL, 2.23 mmol), 8-hydroxyquinoline-2-carbaldehyde (0.2446 g, 1.41 mmol), and NaBH(OAc)$_3$ (0.3932 g, 1.86 mmol). The flask was equipped with a drying tube, and the yellow-orange suspension was stirred at room temperature (RT). After 18 hours, the pale-yellow suspension was quenched with acetone (6 mL) and concentrated at 35° C. under reduced pressure to yield a cloudy, pale-yellow oil containing white precipitate. ESI-MS m/z: 569.29739; calcd for [M+H]$^+$, 569.29698.

The crude oil was dissolved in 6 M HCl (16 mL), and the resulting bright-yellow solution was heated at 90° C. overnight. The solvent was removed under reduced pressure at 60° C., and the yellow residue was taken up in 10% $CH_3CN$/1-20 containing 0.1% TFA (6 mL). The slight suspension was filtered, and the filtrate was purified by reverse-phase preparative HPLC using method B. Pure fractions were combined and concentrated at 60° C. under reduced pressure. To prepare the hydrochloride salt, the residue was thrice redissolved in 6 M HCl (3 mL each) and concentrated under reduced pressure. The product was then twice redissolved in $H_2O$ (3 mL each) and concentrated to remove any excess acid. Lyophilization afforded the title compound (macropaquin) as a bright-yellow solid (0.3685 g, 57% overall yield). Batch-to-batch variation was observed in the number of chloride counteranions per ligand; both trihydrochloride and tetrahydrochloride salts were isolated, as confirmed by potentiometric titration (below) and elemental analysis. No differences were observed in the data obtained from either salt form. $^1$H NMR (500 MHz, DMSO-d$_6$) δ=11.18 (br m, 2H), 10.14 (br s, 1H), 8.43 (d, J=8.5 Hz, 1H), 8.14 (t, J=7.6 Hz, 1H), 8.10 (dd, J=7.8, 1.1 Hz, 1H), 7.93 (dd, J=7.5, 1.2 Hz, 1H), 7.64 (d, J 8.5 Hz, 1H), 7.50 (t, J==7.8 Hz, 1H), 7.45 (dd, J=8.2, 1.3 Hz, 1H), 7.15 (dd, J=75, 1.3 Hz, 1H), 4.96 (s, 2H), 4.77 (s, 2H), 3.93 (m, 8H), 3.61-3.53 (m, 16H). $^{13}$C{$^1$H} NMR (126 MHz, DMSO-d$_6$) δ 165.35, 153.15, 151.03, 149.89, 147.23, 139.29, 137.71, 136.65, 128.13, 127.97, 127.95, 124.29, 120.72, 117.56, 111.95, 69.17, 64.76, 64.63, 57.84, 56.68, 54.20, 53.48. Only 22 distinct signals are detected in the spectrum. Two carbons most likely comprise the signal at 69.17 ppm. $^{19}$F NMR (470 MHz, DMSO-d$_6$): no peaks, confirming the absence of TFA. Elemental analysis found: C, 49.57; H, 6.23; N, 7.94. Calc. for $C_{29}H_{38}N_4O_7.3HCl.2H_2O$: C, 49.76; H, 6.48; N, 8.00. HPLC $t_R$=19.166 min (Method A). DART-MS m/z: 555.28091; calcd for [M+H]$^+$, 555.28133.

Synthesis of macroquin-SO$_3$ (2,2'-((1,4,10,13-tetraoxa-7,16-diazacyclooctadecane-7,16-diyl)bis (methylene))bis(8-hydroxyquinoline-5-sulfonic acid))

The structure of macroquin-SO$_3$ is shown in FIG. 1. An exemplary scheme for synthesizing macroquin-SO$_3$ is provided in FIG. 2. The ligand was synthesized using a modified literature procedure (N. Su et al., *J. Org. Chem.*, 64, 8855-8861, 1999). To an orange solution of 4,13-diaza-18-crown-6 (0.6611 g, 2.52 mmol) and 8-hydroxyquinoline-2-carbaldehyde (0.959 g, 5.54 mmol) in dry 1,2-dichloroethane (50 mL) was added NaBH(OAc)$_3$ (1.609 g, 7.59 mmol). The flask was fitted with a drying tube, and the orange suspension was stirred at RT. After 19 hours, saturated NaHCO$_3$ (20 mL) was added to the pale-yellow suspension to quench the reaction, and the mixture was extracted with CHCl$_3$ (100 mL). The organic layer was concentrated on the rotary evaporator at 40° C. to give an orange oil (1.4958 g), which was used without further purification.

To the crude oil at 0° C. was Slowly added chlorosulfonic acid (10 mL). The resulting orange solution was removed from the ice bath, stirred at RT for 2 hours and 40 minutes, and carefully poured into an Erlenmeyer flask (250 mL) filled with crushed ice over the course of 7 minutes. The bright-yellow slurry was stirred overnight and then concentrated at 60° C. on the rotary evaporator to a yellow-orange liquid. The pH of the liquid was adjusted to approximately 12 using a combination of concentrated aqueous NaOH (2 M) and NaOH pellets, and then filtered through a nylon membrane (0.22 m). The yellow-orange filtrate (~100 mL) was acidified with concentrated (37%) HCl to pH 1-2. The resulting suspension was centrifuged, and the pellet was washed twice with 1 M 1HCl to furnish an off-white solid. The solid was then recrystallized twice by dissolving it in aq. NaOH (2 M) and acidifying to pH 1-2 with concentrated HCl to induce re-precipitation. Each time, the suspension was centrifuged and the pellets were washed with cold H$_2$O. Lyophilization of the isolated solid provided macroquin-SO$_3$ as a pale-yellow powder (0.6032 g, 30% overall yield). $^1$H NMR (500 MHz, DMSO-d$_6$) δ=9.93 and 9.89 (2 overlapping br s, 2H), 9.24 (d, J=8.8 Hz, 1H), 7.88 (d, J=8.0 Hz, 1H), 7.65 (d, J=8.8 Hz, 1H), 7.07 (d, J=8.0 Hz, 1I-), 4.93 (s, 211), 3.87 (br t, J=4.8 Hz, 4Il), 3.65 (br t, J=4.9 Hz, 4Il), 3.45 (s, 4H). $^{13}$C{$^1$H} NMR (126 MHz, DMSO-d$_6$) δ 153.20, 149.28, 137.90, 136.44, 135.18, 126.39, 124.44, 120.41, 109.62, 69.21, 64.76, 57.85, 54.34. Elemental analysis found: C, 47.95; H, 5.66; N, 6.99; Cl, 0.81. Calc for C$_{32}$H$_4$N$_4$O$_{12}$S$_2$.3H$_2$O.0.2HCl: C, 48.16; H, 5.83; N, 7.02; Cl, 0.89. HPLC t$_R$=14.660 (Method A). ESI-MS m/z: 737.21652; calcd for [M+H]$^+$, 737.21569.

Synthesis of Barium Complex of Macropa, i.e., [Ba(Hmacropa)]ClO$_4$

The structure of [Ba(Hmacropa)]$^+$ is shown in FIG. 1. To a suspension of macropa.2HCl.4H$_2$O (0.0230 g, 0.034 mmol) in 2-propanol (0.7 mL) was added triethylamine (20.2 L, 0.145 mmol). The colorless solution was heated at reflux for 25 min before a solution of Ba(ClO$_4$)$_2$.3H$_2$O (0.0150 g, 0.038 mmol) in 2-propanol (0.65 mL) was added dropwise. A precipitate formed immediately. The white suspension was stirred at reflux for 1 hour before it was cooled and centrifuged. The supernatant was removed, and the pellet was washed with 2-propanol (2×0.2 mL) and air-dried on glassine paper. The title complex was isolated as a white powder (0.0206 g) containing a minor amount of residual triethylamine salt and 2-propanol. $^1$H NMR (600 MHz, CD$_3$OD basified with 2 M NaOH to pD/H~11 by litmus) δ=7.70 (td, J=7.6, 1.0 Hz, 2H), 7.64 (d, J=7.7 Hz, 2H), 7.31 (d, J=7.6 Hz, 2H), 5.23 (d, J=14.4 Hz, 2H), 4.65 (t, J=11.0 Hz, 2H), 3.98 (q, J=11.5 Hz, 4H), 3.90 (t, J=10.6 Hz, 2H), 3.53-3.48 (m, 4H), 3.44 (d, J=10.0 Hz, 2H), 3.35-3.28 (m, 4H partially overlapping with CD$_3$OD peak), 3.24 (d, J=10.6 Hz, 2H), 2.69 (td, J=13.8, 3.2 Hz, 2H), 2.44 (d, J=14.0 Hz, 2H), 2.15 (d, J=13.8 Hz, 2H). $^{13}$C{$^1$H} NMR (126 MHz, CD$_3$OD basified with 2 M NaOH to pD/H~11 by litmus) δ=172.12, 159.07, 154.70, 138.92, 125.73, 123.12, 71.73, 71.40, 69.17, 68.87, 61.20, 56.13, 55.83. ESI-MS m/z: 669.15166 and 335.07930; calcd for [C$_{26}$H$_{35}$BaN$_4$O$_8$] and [C$_{26}$H$_{36}$BaN$_4$O$_8$]$^{2+}$, respectively: 669.15018 and 335.07873.

Synthesis of Barium Complex of Macropaquin, i.e., [Ba(Hmacropaquin)]ClO$_4$

The structure of [Ba(Hmacropaquin)]$^+$ is shown in FIG. 1. To a suspension of macropaquin.4.2HCl.1.5H$_2$O (0.096 g, 0.131 mmol) in 2-propanol (2 mL) was added triethylamine (109.2 μL, 0.784 mmol). The suspension was heated at reflux for 25 minutes, giving a pale-yellow solution to which a solution of Ba(ClO$_4$)$_2$.3H$_2$O (0.0541 g, 0.139 mmol) in 2-propanol (1.5 mL) was added dropwise. A precipitate formed immediately. The yellow-brown suspension was stirred at reflux for 1.5 hours and then it was cooled, divided into three portions, and centrifuged. The supernatant was removed, and each pellet was washed with 2-propanol (2×0.350 mL), combined, and dried under reduced pressure to give the title complex as a pale-tan powder (0.0640 g) containing residual triethylamine salt and 2-propanol. $^1$H NMR (600 MHz, CD$_3$OD basified with 2 M NaOH to pD/H~11 by litmus) δ=7.86 (d, J=8.4 Hz, 1H), 7.49 (t, J=7.7 Hz, 1H), 7.28 (d, J=7.8 Hz, 1H), 7.22 (d, J 7.7 Hz, 1H), 7.10 (d, J=8.4 Hz, 1H), 6.84 (t, J=7.8 Hz, 1H), 6.51 (d, J=7.8 Hz, 1H), 6.24 (d, J=7.9 Hz, 1H), 5.12 (d, J=14.4 Hz, 1H), 5.00 (d, J=15.8 Hz, 1H), 4.59 (t, J=10.2 Hz, 1H), 4.53 (t, J=10.7 Hz, 1H), 4.15 (t, J=10.2 Hz, 1H), 4.05 (t, J=11.0 Hz, 1H), 3.98-3.88 (m, 3H), 3.85 (1, J=10.4 Hz, 1H), 3.70-3.58 (m, 2H), 3.57-3.49 (m, 4H), 3.49-3.39 (m, 3H), 3.39-3.31 (m, 2H), 3.29-3.17 (m, 2H), 2.81-2.72 (m, 1H), 2.68 (d, J=13.9 Hz, 1H), 2.48 (d, J=13.9 Hz, 1H), 2.22 (d, J=13.4 Hz, 1H), 2.17 (d, J=13.6 Hz, 1H). $^{13}$C{$^1$H} NMR (126 MHz, CD$_3$OD basified with 2 M NaOH to pD/H~11 by litmus) δ=171.67, 167.04, 158.12, 154.60, 154.09, 143.77, 138.75, 138.11, 130.31, 129.23, 125.14, 122.70, 120.09, 114.58, 110.14, 71.93, 71.71, 71.55, 69.93, 69.66, 69.52, 62.15, 61.56, 55.56, 55.50, 55.36, 54.14. Only 27 distinct signals were observed in the spectrum. Two carbons most likely comprise each signal at 71.71 ppm and 69.66 ppm. ESI-MS m/z: 691.17227 and 346.08969; calcd for [C$_{29}$H$_{37}$BaN$_4$O$_7$]$^+$ and [C$_{29}$H$_{38}$BaN$_4$O$_7$]$^+$, respectively, 691.17092 and 346.08910.

X-Ray Diffraction Studies

Crystals of [Ba(Hmacropa)(DMF)]ClO$_4$.Et$_2$O were grown via vapor diffusion of Et$_2$O into a DMF solution of the isolated complex at 4° C. After 10 days, the inner vial was removed, capped, and stored at 4° C. for 2 months to produce single crystals suitable for X-ray diffraction. Single crystals of [Ba(Hmacropaquin)(DMF)]ClO$_4$.DMF were obtained following vapor diffusion of petroleum ether into a DMF solution of the isolated complex. Single crystals of [Ba(H$_2$macroquin-SO$_3$)(H$_2$O)].4H$_2$O were isolated from a capped solution of ligand (99.2 m) and BaNO$_3$ (99.2 m, from ICP standard) in 10 mM MOPS buffer (pH 7.4, 1=100 mM NMe$_4$Cl) after 2 days.

Low-temperature X-ray diffraction data for crystals of [Ba(Hmacropaquin)(DMF)]ClO$_4$ and [Ba(H$_2$macroquin-SO$_3$)(H$_2$O)].4H$_2$O were collected on a Rigaku XTALAB® Synergy diffractometer coupled to a Rigaku Hypix® detector with Cu Kα radiation (λ=1.54184 Å), from a PhotonJet micro-focus X-ray source at 100 K. The diffraction images were processed and scaled using appropriate software. Low-temperature X-ray diffraction data for [Ba(Hmacropa)(DMF)]ClO$_4$·Et$_2$O were collected on a Bruker® APEX 2 CCD Kappa diffractometer (Mo Kα λ=0.71073 Å) at 223 K. The diffraction images were processed and scaled using appropriate software.

[Ba(Hmacropa)(DMF)]ClO$_4$·Et$_2$O crystallizes as a racemic twin [BASF=0.406(14)]. The structures were solved by intrinsic phasing using SHELXT (Sheldrick, G. M. Acta Crystallogr. Sect. A 2015, 71, 3-8.) and refined against F$^2$ on all data by full-matrix least squares with SHELXL (Sheldrick, G. M. Acta Crystallogr. Sect. A 2008, 64, 112-122) following established refinement strategies (Müller, P. Crystallogr. Rev. 2009, 15, 57-83). All non-hydrogen atoms were refined anisotropically. All hydrogen atoms bound to carbon were included in the model at geometrically calculated positions and refined using a riding model. Hydrogen atoms bound to oxygen were located in the difference Fourier synthesis and subsequently refined semi-freely with the aid of distance restraints. The isotropic displacement parameters of all hydrogen atoms were fixed to 1.2 times the Ueq value of the atoms they are linked to (1.5 times for methyl groups). Crystallographic data collection and refinement parameters, bond lengths, and bond angles were collected.

Figures 3A, 3B, 3C, 3D, 3E, 3F:
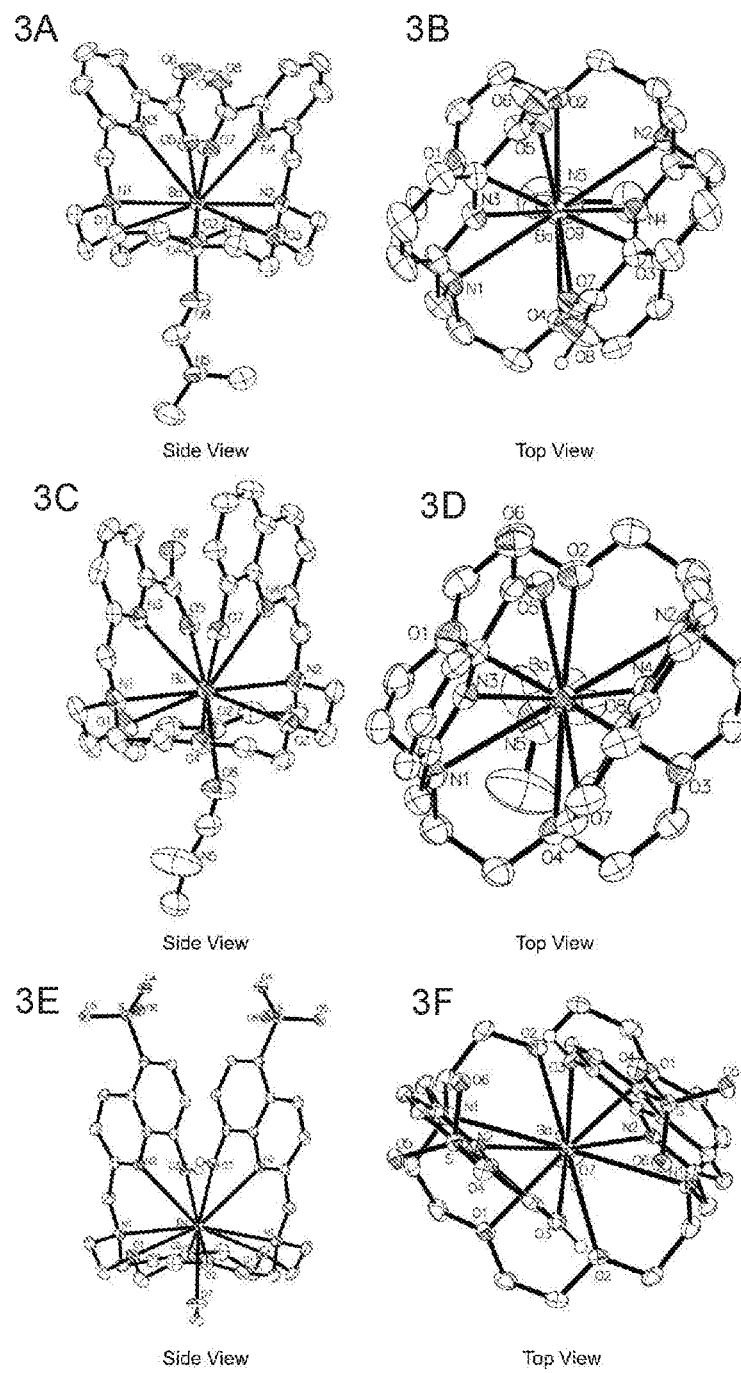
FIGS. 3A-3F are X-ray crystal structures of [Ba(Hmacropa)(DMF)]$ClO_4$·$Et_2O$ (FIGS. 3A, 3B), [Ba(Hmacropaquin)(DMF)]$ClO_4$-DMF (FIGS. 3C, 3D), and [Ba($H_2$macroquin-$SO_3$)($H_2O$)]·$4H_2O$ (FIGS. 3E, 3F). Ellipsoids are drawn at the 50% probability level. Counteranions, non-acidic hydrogen atoms, and outer-sphere solvent molecules are omitted for clarity.

FIGS. 3A-3F are X-ray crystal structures of [Ba(Hmacropa)(DMF)]ClO$_4$·Et$_2$O (FIGS. 3A, 3B), [Ba(Hmacropaquin)(DMF)]ClO$_2$·DMF (FIGS. 3C, 3D), and [Ba(H$_2$macroquin-SO$_3$)(H$_2$O)]·4H$_2$O (FIGS. 3E, 3F). Ellipsoids are drawn at the 50% probability level. Counteranions, non-acidic hydrogen atoms, and outer-sphere solvent molecules are omitted for clarity. In each complex, the Ba$^{2+}$ ion is situated slightly above the diaza-18-crown-6 ring, and the two pendant arms are oriented on the same side of the macrocycle. The coordination sphere of the Ba$^{2+}$ ion comprises all ten donor atoms of each ligand (N$_4$O$_6$), together with an oxygen atom from a coordinated solvent molecule that penetrates each macrocycle from the opposite face.

The ligand conformation, which can be denoted with Δ or Λ to indicate the pendent arm helical twist and δ or λ to indicate the tilt of each five-membered chelate ring, is identical for the three complexes. Each ligand attains the Δ(δλδ)(δλδ) conformation, present in equal amounts with its enantiomer. For complexes of macropa with other large metal ions, this conformation is also the most stable (Roca-Sabio et al., 2009, supra). Protonation of one picolinate arm of macropa and the 8-hydroxyquinoline arm of macropaquin gives rise to complexes of the cationic formulae [Ba(Hmacropa)(DMF)]$^+$ and [Ba(Hmacropaquin)(DMF)]$^+$, respectively. By contrast, macroquin-SO$_3$ forms a neutral complex with Ba$^{2+}$, [Ba(H$_2$macroquin-SO$_3$)(H$_2$O)]. In this case, both phenolates are protonated to form neutral donors, but the sulfonic acid groups exist in the deprotonated anionic form. As reflected by the similar distances between Ba$^{2+}$ and the two nitrogen atoms of each macrocycle, the Ba$^{2+}$ ion is situated symmetrically within the macrocycle of each complex. Collectively, the structural features of these complexes suggest that macropa, macropaquin, and macroquin-SO$_3$ can optimally accommodate the large Ba$^{2+}$ ion.

Thermodynamic Stability Studies by Potentiometric Titration

Potentiometric measurements were carried out using a titrator equipped with a combination electrode and an exchange unit with an automatic burette (10 mL). The titration vessel was fitted with a removable glass cell (~70 mL) and was thermostated at 25° C. using a circulating water bath. CO$_2$ was excluded from the vessel prior to and during the titrations using a small positive pressure of Ar that was passed through a solution of 30 wt % KOH. Carbonate-free KOH (~0.1 M) was prepared by dissolving KOH pellets (semiconductor grade, 99.99% trace metals basis) in freshly boiled water (≥18 MΩ-cm) and was standardized by potentiometric titration against potassium hydrogen phthalate. Hydrochloric acid (0.1 M) was standardized against freshly prepared KOH. Titration solutions were maintained at a constant ionic strength of 0.1 M using KCl (≥99.5%) and were equilibrated for 15 minutes prior to the addition of titrant. Before every titration, the electrode was calibrated in terms of hydrogen ion concentration by titrating a solution of standardized HCl (5 mM) containing supporting electrolyte (95 mM) with standardized KOH (2 mL). Data within the pH ranges of 2.5-3.2 and 10.8-11.2 were analyzed using software to obtain the standard electrode potential (E$_0$) and slope factor. Owing to the sharp rise in pH at the titration endpoint (pH 3.2-10.8), data obtained in this region are subject to significant error and were therefore excluded from the calibration analysis. A pK$_w$ value of 13.78 was taken from the literature (Baes, C. F.; Mesmer, R. E. The Hydrolysis of Cations; Wiley: New York, 1976).

Protonation Constants

Stock solutions of macropa and macropaquin were prepared in H$_2$O. A stock solution of macroquin-SO$_3$ could not be prepared due to the poor aqueous solubility of this ligand; instead, a weighed portion of macroquin-SO$_3$ was used for each titration. The exact ligand concentrations were determined from the potentiometric titration curves with KOH. Protonation equilibria of macropa$^{2-}$ and macropaquin$^{2-}$ were determined by adding standardized KOH to a solution (20 mL) containing ligand (~0.02 mmol), 0.1 M HCl (0.1 mmol), and 1 M KCl (1.9 mmol). The titration method employed a 0.1 mV/min drift limit with a maximum wait time of 90 sec between addition of base and measurement. At least 70 data points were collected over the pH range of 2.5-10.5 (macropa) or 2.5-11.3 (macropaquin). The protonation constants, defined in Eq. 1, were calculated from the average of at least 4 independent titrations using the appropriate software.

$$K_{ai} = \frac{[H_iL]}{[H_{i-1}L][H^+]} \qquad (1)$$

Both ligand (L) and proton concentrations were admitted as refineable parameters. The errors given for the protonation constants correspond to one standard deviation. The protonation constants measured for macropa$^{2-}$ were consistent with those previously reported (Roca-Sabio et al., 2009, supra); log K$_{a5}$ was not able to be determined under the conditions employed here. Protonation equilibria of macroquin-SO$_3^{4-}$ were determined by titrating standardized HCl (~5.19 mL) into a solution (62.5 mL) containing ligand (~0.013 mmol, 10.4 mg), KOH (0.25 mmol), and 1 M KCl (6 mmol). The same titration method was employed as described above for the other two ligands. At least 90 data points over the pH range of 4.0-10.8 were included in the refinement; no additional protonation constants could be refined when data from pH 2.5-3.99 were included. The protonation constants were calculated from the average of 15 independent titrations.

Stability Constants

ICP standards of calcium, strontium, and barium in dilute HNO$_3$ were employed in the titrations. The exact amount of HNO$_3$ was determined by potentiometric titration of each metal solution (1 mL), diluted to a known volume with H$_2$O, with standardized KOH to pH ~7; under these conditions, no precipitation of metal hydroxide species was observed. The data were analyzed using a Gran plot (Gran, G. Analyst 1952, 77, 661-671). Stability constants were measured for the alkaline earth complexes of macropa$^{2-}$ and macropaquin$^{2-}$ by adding standardized KOH to a solution (20 mL) containing ligand (0.02 mmol), metal (0.02 mmol), 1 M KCl (1.9 mmol), and a portion of 0.1 M HCl sufficient to bring the total acid content (HCl+HNO$_3$) to 0.1 mmol. The titration method employed either a 0.1 mV/min or 0.2 mV/min drift limit with a maximum wait time of 300 seconds between addition of base and measurement. Implementing a minimum wait time (e.g. 60 sec) did not change the values of the calculated stability constants. Data points (~30-90) obtained over the pH ranges of 2.5-10.5 (Ba-macropa), 2.8-10.5 (Sr-macropa), 4.0-10.5 (Ca-macropa), 2.7-11.3 (Ba-macropaquin), and 4.0-11.3 (Sr- and Ca-macropaquin) were included in the refinements. These pH ranges reflect the portion of the titration curves in which metal binding is occurring. Using the protonation constants measured for each ligand, the stability constants (Equations 2-4, below) were calculated from the average of at least 3 independent titrations using appropriate software. Proton concentration was admitted as a refineable parameter. Ligand (L) concentration was taken as the averaged value obtained from the refinements of ligand-only titrations. The errors given for the stability constants correspond to one standard deviation.

$$K_{ML} = \frac{[ML]}{[M][L]} \quad (2)$$

$$K_{MHL} = \frac{[MHL]}{[ML][H]} \quad (3)$$

$$K_{MH_2L} = \frac{[MH_2L]}{[MHL][H]} \quad (4)$$

The alkaline earth stability constants for macroquin-SO$_3^{4-}$ were determined using a system in which each ligand titration was paired with a ligand-metal titration. These pairwise titrations permitted the ligand concentration for the metal-ligand titrations to be known with reasonable certainty from the refinement of the ligand-only titrations. Immediately following a titration of the free ligand with HCl, metal ion (0.013 mmol) was added and the solution was equilibrated under Ar for 15 minutes before the addition of standardized KOH. The same titration method was employed as described above for macropa$^{2-}$ and macropaquin$^{2-}$. Approximately 80-100 data points over the pH ranges of 3.5-10.5 (Ba), 4-10.5 (Sr), and 6-10.5 (Ca) were included in the refinements. Stability constants were calculated as described above. Although the inclusion of a CaH$_2$L species in the model for the macroquin-SO$_3$ titrations with Ca$^{2+}$ resulted in reduced sigma values and lower residuals, the refined concentration of this species was deemed insufficient (<10%) for the accurate determination of log K$_{CaH2L}$. Owing to the very low concentrations of metal and macroquin-SO$_3$ employed in these titrations, the error associated with the calculated stability constants may be slightly higher than is reflected by the standard deviations of the measurements.

Log conditional constants (log K') of the alkaline earth complexes at pH 7.4 were calculated using the experimentally determined protonation and stability constants. These constants are expressed by the following equation:

$$K' = \frac{[(ML)']}{[M][H_nL]}$$

In the above equation, [(ML)']=[ML]+[MHL]+[MH$_2$L], and [H$_n$L]=[L], [HL], [H$_2$L] ... [H$_n$L].

To further evaluate the coordination properties of the ligands with the AEs, their protonation constants and the stability constants of their Ca$^{2+}$, Sr$^{2+}$, and Ba$^{2+}$ complexes were measured by potentiometric titration in 0.1 M KCl (Table 1 below). For comparison, corresponding values for DTPA and DOTA, the current state of the art for Ba$^{2+}$ chelation, are also provided.

TABLE 1

Protonation Constants of macropa$^{2-}$, macropaquin$^{2-}$, and macroquin-SO$_3^{4-}$ and Thermodynamic Stability Constants of Their Alkaline Earth Complexes Determined by pH-Potentiometry (25° C. and I = 0.1M KCl).a

|  | macro-pa$^{2-}$ | macro-paquin$^{2-}$ | macroquin-SO$_3^{4-}$ | DOTA$^{4-b}$ | DTPA$^{5-c}$ |
|---|---|---|---|---|---|
| log K$_{a1}$ | 7.41(1) (7.41)$^d$ | 10.33(4) | 9.34(4) | 11.14 | 10.34 |
| log K$_{a2}$ | 6.899(3) (6.85) | 7.15(3) | 9.43(1) | 9.69 | 8.59 |
| log K$_{a3}$ | 3.23(1) (3.32) | 6.97(2) | 6.75(4) | 4.85 | 4.25 |
| log K$_{a4}$ | 2.45(5) (2.36) | 3.24(4) | 6.62(4) | 3.95 | 2.71 |
| log K$_{a5}$ | (1.69) |  |  |  | 2.18 |
| log K$_{CaL}$ | 5.79(1) [5.25]$^e$ | 5.90(4) | 6.04(8) | 16.37 | 11.77 |
| log K$_{CaHL}$ |  | 8.59(2) | 8.60(4) | 3.60 | 6.10 |
| log K$_{CaH2L}$ |  |  |  |  |  |
| log K$_{SrL}$ | 9.442(4) [9.57] | 9.19(5) | 8.62(2) | 14.38 | 9.68 |
| log K$_{SrHL}$ | 3.35(8) [4.16] | 8.92(2) | 8.34(4) | 4.52 | 5.4 |
| log K$_{SrH2L}$ |  |  | 6.920(3) |  |  |
| log K$_{BaL}$ | 11.11(4) | 10.87(2) | 10.44(6) | 11.75 | 8.78 |
| log K$_{BaHL}$ | 3.76(2) | 9.76(2) | 9.24(7) |  | 5.34 |
| log K$_{BaH2L}$ | 2.49(7) | 3.28(2) | 7.80(2) |  |  |
| log K'$_{Ca}{}^f$ | 5.42 | 3.94 | 3.19 | 10.34 | 7.63 |
| log K'$_{Sr}{}^f$ | 9.07 | 7.54 | 5.64 | 8.35 | 5.53 |
| log K'$_{Ba}{}^f$ | 10.74 | 10.05 | 8.76 | 5.72 | 4.63 |
| pCa$^g$ | 6.54 | 6.04 | 6.01 | 11.29 | 8.59 |
| pSr$^g$ | 10.02 | 8.50 | 6.70 | 9.30 | 6.61 |
| pBa$^g$ | 11.69 | 11.01 | 9.72 | 6.76 | 6.15 | aData reported previously for DOTA$^{4-}$ and DTPA$^{5-}$ are provided for comparison.
$^b$Clarke, E. T. et al., Inorg. Chim. Acta 1991, 190, 27-36, I = 0.1M KCl.
$^c$Protonation constants and log K$_{CaL}$ from Schmitt-Willich, H. et al., Inorg. Chem. 1999, 38, 1134-1144, I = 0.1M KCl. Other values from Martell, A. E.; Smith, R. M. Critical Stability Constants: Vol. 1; Plenum Press: New York; London, 1974.
$^d$Parenthetic values from Roca-Sabio, A. et al., J. Am. Chem. Soc. 2009, 131, 3331-3341, I = 0.1M KCl.
$^e$Bracketed values from Ferreirós-Martinez, R. et al., Inorg. Chem. 2011, 50, 3772-3784, I = 0.1M KNO$_3$.
$^f$Conditional stability constant at pH 7.4, 25° C., and I = 0.1M KCl.
$^g$Calculated from −log [M$^{2+}$]$_{free}$ ([M$^{2+}$] = 10$^{-6}$M; [L] = 10$^{-5}$M; pH 7.4; 25° C.; I = 0.1M KCl).

A comparison of the ligand protonation constants reveals that sequential replacement of each picolinate arm of macropa by 8-hydroxyquinoline-based binding groups significantly decreases the basicity of the nitrogen atoms of the macrocyclic core to which they are attached. This trend is evidenced by the lower amine protonation constants of 7.15 (log K$_{a2}$) and 6.97 (log K$_{a3}$) for macropaquin and 6.75 (log $K_{a3}$) and 6.62 (log $K_{a4}$) for macroquin-$SO_3$, versus 7.41 (log $K_{a1}$) and 6.899 (log $K_{a2}$) for macropa. A comparison between related ethylenediamine-derived ligands bearing either picolinate or 8-hydroxyquinoline groups also shows that the basicity of the secondary amines is lower when attached to the latter (Boros, E. et al. *J. Am. Chem. Soc.* 2010, 132, 15726-15733). The electron-withdrawing sulfonate groups on macroquin-$SO_3$ give rise to more acidic phenols (log $K_{a1}$, =9.34, log $K_{a2}$=9.43) compared to macropaquin (log $K_{a1}$=10.33). Notably, the second protonation constant of macroquin-$SO_3$ is slightly larger than the first protonation constant. This apparent reversal in expected values may be attributed to intramolecular hydrogen bonding that slightly stabilizes the second proton; upon its removal, the hydrogen bond network is broken, and the final remaining proton becomes more acidic.

Because protons compete with metal ions for binding sites on ligands, ligand basicity is an important factor that contributes to the affinity of a ligand for a metal ion at a specific pH. The overall basicity of the ligands, taken as the sum of their log $K_a$ values, follows the order macropa (19.99) <macropaquin (27.69)<macroquin-$SO_3$ (32.14). The speciation of the ligands reflects these overall basicity values. At pH 7.4, 43% of macropa is fully deprotonated ($L^{2-}$), consistent with the low overall basicity of this ligand. By contrast, fully deprotonated macropaquin$^{2-}$ and macroquin-$SO_3^{4-}$ do not exist in solution below pH 8. At pH 7.4, the monoprotonated species of macropaquin, $HL^-$, predominates (56%), whereas macroquin-$SO_3$ is mostly present as $H_2L^{2-}$ (78%). On the basis of these results, macropaquin and macroquin-$SO_3$ may chelate metal ions less effectively than macropa near neutral pH due to greater competition with protons for binding.

With the protonation constants in hand, the stability constants of these ligands with $Ca^{2+}$, $Sr^{2+}$ and $Ba^{2+}$ were determined. Remarkably, macropa, macropaquin, and macroquin-$SO_3$ all exhibit significant thermodynamic preferences for large over small AEs; the measured log $K_{ML}$ values are highest for complexes of $Ba^{2+}$ and lowest for complexes of $Ca^{2+}$. However, the affinities of the ligands for $Ba^{2+}$ and $Sr^{2+}$ decrease as the picolinate arms on the macrocyclic scaffold are replaced with 8-hydroxyquinoline or 8-hydroxyquinoline-5-sulfonic acid arms. For example, log $K_{BaL}$ values of 11.11, 10.87, and 10.44 were measured for complexes of macropa, macropaquin, and macroquin-$SO_3$, respectively, containing zero, one, and two 8-hydroxyquinoline-based pendent arms. This trend signifies that 8-hydroxyquinoline-based pendent arms may not be suitable metal-binding groups for the chelation of large metal ions such as $Ba^{2+}$.

The speciation diagrams for solutions of $Ba^{2+}$ and the three ligands, based on the thermodynamic constants in Table 1, are shown in FIGS. 4A-4E. More specifically, FIGS. 4A-4E show species distribution diagrams of macropa (FIG. 4A), macropaquin (FIG. 4B), macroquin-$SO_3$ (FIG. 4C), DOTA (FIG. 4D), and DTPA (FIG. 4E) in the presence of $Ba^{2+}$ at $[Ba^{2+}]_{tot}=[L]_{tot}=1.0$ mM, I=0.1 M KCl, and 25° C. Refinement of the potentiometric titration data also revealed the presence of protonated metal complexes, or MHL and $MH_2L$ species, for all three ligands bound to $Ca^{2+}$, $Sr^{2+}$, and $Ba^{2+}$. The inclusion of these species within the solution phase model is consistent with the results from X-ray crystallography, which also identified these species in the solid state. The major species present at pH 7.4 is the ML species for macropa, the MHL species for macropaquin, and the $MH_2L$ species for macroquin-$SO_3$. These data indicate that the 8-hydroxyquinoline donors retain their basicity when bound to the $Ba^{2+}$ ion. The presence of two such donors in macroquin-$SO_3$ gives rise to the large prevalence of the protonated complex $MH_2L$ near neutral pH.

In comparing the thermodynamic properties of these ligands to the commonly employed ligands DOTA and DTPA, it is noteworthy that the log $K_{BaL}$ value of 11.11 for macropa is substantially larger than that for DTPA (8.78) and only 0.64 log units lower than that for DOTA, indicating that macropa is a high-affinity ligand for $Ba^{2+}$. A more accurate reflection of thermodynamic affinity in aqueous solution, however, can be expressed using conditional stability constants, which account for the effect of protonation equilibria of the ligands on complex stability (Alberty, R. A. *Eur. J. Biochem.* 19%, 240, 1-14). The conditional stability constants (log K') of the AE complexes at pH 7.4 are given in Table 1. The log $K'_{Ba}$ value of 10.74 for macropa is 5-6 orders of magnitude greater than those for DOTA (5.72) and DTPA (4.63). Macropa also exhibits higher affinity for $Ba^{2+}$ at pH 7.4 than macropaquin (log K'=10.05) and macroquin-$SO_3$ (log K'=8.76). From these values, macropa emerges as remarkably superior to all other ligands for the chelation of $Ba^{2+}$ at near-neutral pH.

Figure 4A:
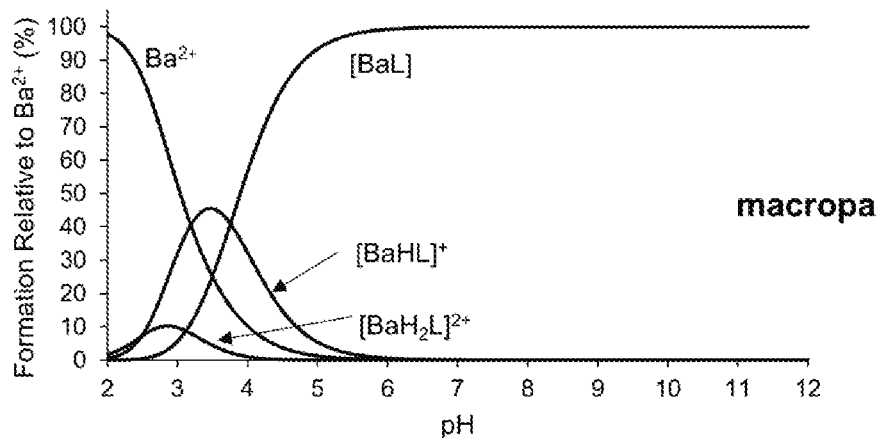
FIGS. 4A-4E show species distribution diagrams of macropa (FIG. 4A), macropaquin (FIG. 4B), macroquin-$SO_3$ (FIG. 4C), DOTA (FIG. 4D), and DTPA (FIG. 4E) in the presence of $Ba^{2+}$ at $[Ba^{2+}]_{tot}=[L]_{tot}=1.0$ mM, I=0.1 M KCL, and 25° C., where "L" indicates "ligand" (i.e., metal-chelating molecule).
Figure 4B:
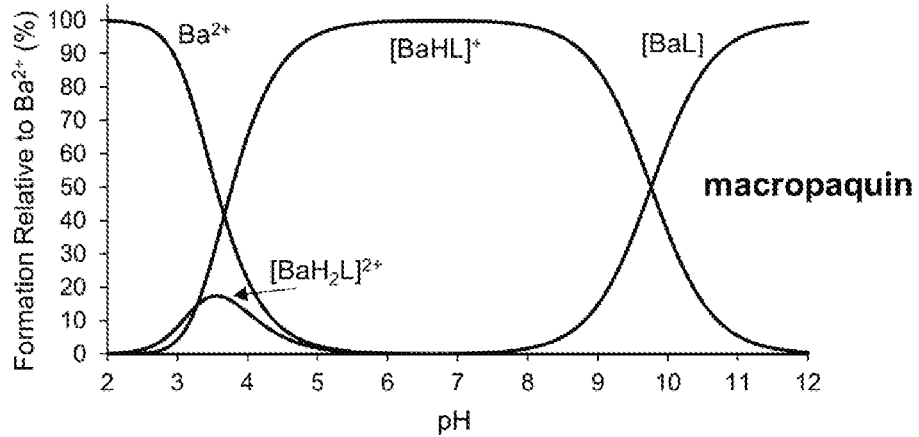
Figure 4C:
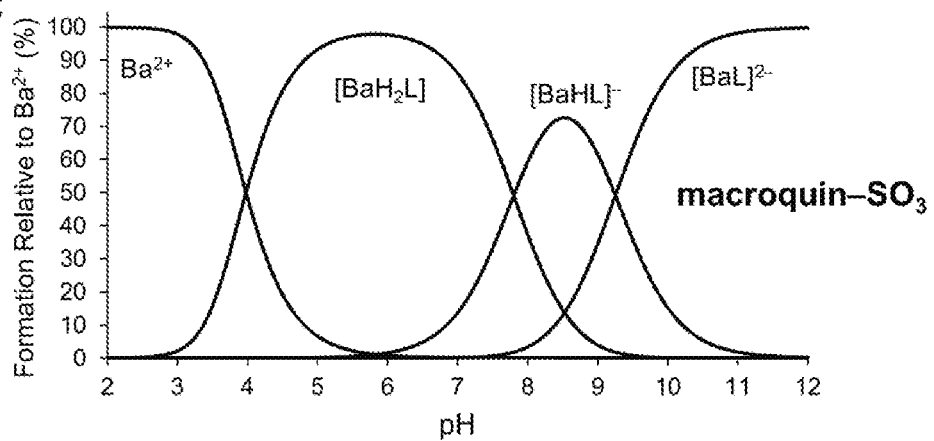
Figure 4D:
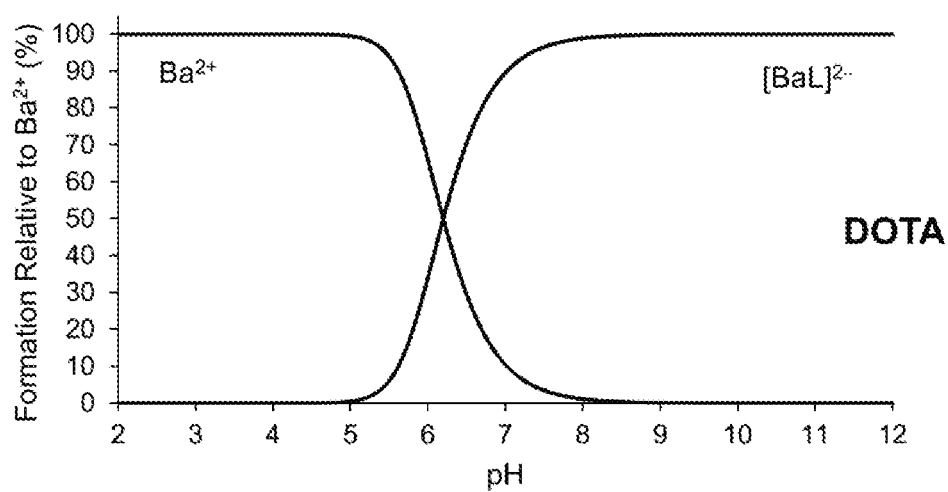
Figure 4E:
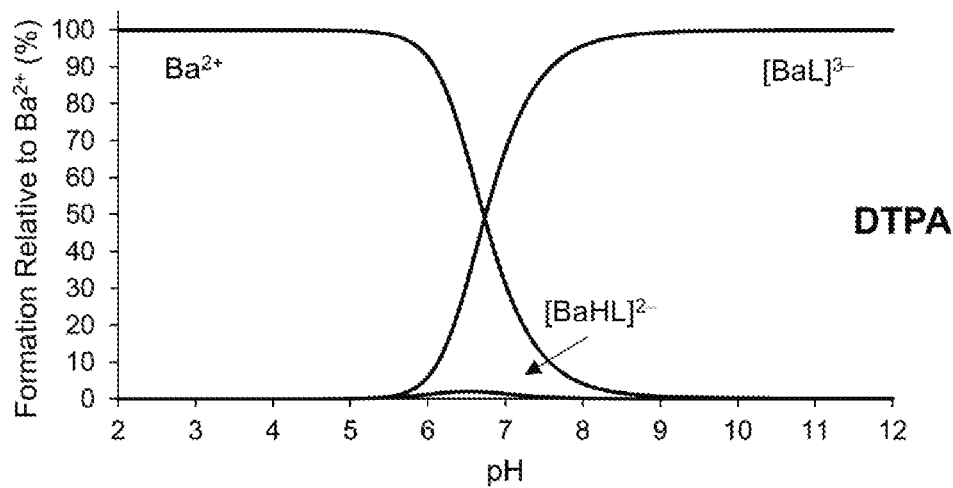

Another measure of conditional thermodynamic affinity of a ligand for a metal ion is provided by pM values (Table 1), which are defined as the negative log of the free metal concentration in a pH 7.4 solution containing $10^{-6}$ M metal ion and $10^{-5}$ M ligand (Harris, W. R.; Carrano, C. J.; Raymond, K. N. *J. Am. Chem. Soc.* 1979, 101, 2722-2727). Larger pM values correspond to higher affinity chelators because they indicate that there is a smaller concentration of free metal ions under these conditions at equilibrium. The pBa values of DOTA and DTPA are only 6.76 and 6.15, respectively, reflecting the presence of a significant amount of free $Ba^{2+}$ at pH 7.4 (FIGS. 4D and 4E). By contrast, 90% of $Ba^{2+}$ is already bound by macropa at pH 4.0 and 99% is complexed at pH 5.1, consistent with the high pBa value of 11.69 for this ligand. Furthermore, macropa is 1.17-fold and 1.79-fold more selective for $Ba^{2+}$ over $Sr^{2+}$ and $Ca^{2+}$, respectively, as determined by the ratio of the corresponding pM values. By contrast, these selectivity values are <1 for DOTA and DTPA, emphasizing their poor affinities for the large $Ba^{2+}$ ion at pH 7.4.

Having demonstrated that macropa chelates $Ba^{2+}$ with high thermodynamic stability and selectivity, the kinetic inertness of this complex was examined in comparison to that of macropaquin and macroquin-$SO_3$. The Ba-L complexes were first challenged with 1000 equiv of $La^{3+}$, a metal that forms a complex of high thermodynamic stability with macropa (log $K_{LaL}$=14.99) (Roca-Sabio et al. 2009, supra). The substitution of $Ba^{2+}$ with $La^{3+}$ was monitored at RT and pH 7.3 by UV-vis spectrophotometry. Ba-macropa and Ba-macropaquin exhibited moderate stability, giving rise to similar half-lives of 5.45±0.20 min and 6.07±0.13 min, respectively. By contrast, Ba-macroquin-$SO_3$ underwent transmetalation with $La^{3+}$ much more rapidly ($t_{1/2}$=0.65±0.05 min), indicating that macroquin-$SO_3$ cannot adequately retain $Ba^{2+}$ under these conditions.

Complex Stability: Transmetalation Challenges $La^{3+}$ Transmetalation Studies

The pH of a 100 mM 3-(N-morpholino)propanesulfonic acid (MOPS) buffer (I=1 M $NMe_4Cl$) was adjusted to 7.3 using aqueous $NMe_4OH$. A stock solution of $LaCl_3.6.8H_2O$ (310 mM) was made fresh daily in 5 mM HCl. Stock solutions of macropa (28.88 mM) and macropaquin (18.53 mM) were prepared in $H_2O$. A stock solution of macroquin-$SO_3$ (7.39 mM) was prepared in MOPS buffer by adding aqueous $NMe_4OH$ dropwise until all solid was dissolved.

Stock solutions of complexes were prepared in situ in MOPS buffer using equimolar (59 μM) ligand and Ba(NO$_3$)$_2$ (1001 μg/mL ICP standard) and were equilibrated for at least 5 minutes prior to use. Transmetalation challenges were initiated by adding 478 μL (1000-fold excess) of LaCl$_3$ to a cuvette containing 2522 μL of Ba-L complex. The cuvette was inverted 3×, and then UV-vis spectra were acquired every 15 or 30 sec until there were no further spectral changes (20-90 min). The final pH of each solution was between 7.23 and 7.36. Pseudo first-order rate constants ($k_{obs}$) were calculated from the slopes of the plots of ln($A_\infty-A_t$) versus time for each complex using linear regression. $A_\infty$ is the final absorbance value and $A_t$ is the absorbance value at time t at 284 nm, 264 nm, or 368 nm, wavelengths corresponding to the appearance of the La$^{3+}$ complexes of macropa, macropaquin, and macroquin-SO$_3$, respectively. Half-lives ($t_{1/2}$) were calculated using the equation $t_{1/2}=0.693/k_{obs}$ and are reported as the mean of three replicates±1 standard deviation. In control experiments, a solution containing Ba-L (2522 μL) and 5 mM HCl (478 μL) was monitored for 20-90 min by UV-vis spectrophotometry. No spectral changes were observed for any of the complexes under these conditions, confirming that the Ba-L complexes do not undergo dissociation over the time course of the experiments.

Hydroxyapatite Challenges

Because Ba$^{2+}$ possesses bone-seeking properties, the stability of the Ba$^{2+}$ complexes in the presence of hydroxyapatite (Ca$_5$(PO$_4$)$_3$(OH), HAP), the predominant mineral that comprises bone, was also evaluated. HAP was suspended in solutions containing the complexes formed in situ (1.1 equiv L, 1.0 equiv Ba$^{2+}$) in pH 7.6 buffer, and the amount of Ba$^{2+}$ remaining in the liquid phase, reflecting intact Ba-L complex, was determined by graphite furnace atomic absorption spectroscopy (GFAAS). Whereas free Ba$^{2+}$ is adsorbed by HAP in less than 10 min, Ba-macropa and Ba-macropaquin respectively retained 82% and 68% of this ion after 20 h. Ba-macroquin-SO$_3$ displayed the least stability in the presence of HAP, with only 17% of the complex remaining intact after 20 h. Taken together, the results of these challenges demonstrate that Ba-macropa and Ba-macropaquin are considerably more stable than Ba-macroquin-SO$_3$ under extreme conditions of large excesses of competing metal ions. This feature may be important for Ba$^{2+}$ chelation in industrial applications, such as scale dissolution, because numerous other metal ions are present during these processes. The inferior kinetic stability of Ba-macroquin-SO$_3$ relative to the other two complexes correlates with the lower thermodynamic affinity of this ligand for Ba$^{2+}$ and is most likely a consequence of the fact that the diprotonated Ba$^{2+}$ complex of macroquin-SO$_3$, BaH$_2$L, is the major species at pH 7.4 (FIG. 4C). This complex is expected to be substantially more labile than the ML species due to decreased electrostatic interactions between the ion and ligand.

More specifically, hydroxyapatite (HAP, Ca$_5$(PO$_4$)$_3$(OH)) challenges were carried out in 500 mM Tris buffer. The pH of the buffer was adjusted to 7.6 using concentrated HCl. Stock solutions of macropa (19.34 mM) and macropaquin (19.00 mM) were prepared in water. The concentrations of these stocks were verified by quantitative NMR (n=2 for each ligand) using two independently prepared standards of potassium hydrogen phthalate in D$_2$O. Macroquin-SO$_3$ (14.3 mg) was suspended in water, and sufficient aqueous NMe$_4$OH was added to dissolve the solid. The concentration of macroquin-SO$_3$ was determined by UV-vis spectrophotometry from the average of two titrations with Ba$^{2+}$. Two independent titrants containing Ba$^{2+}$ (final concentration of 1.67 mM, using 1001 μg/mL ICP standard) and macroquin-SO$_3$ (18 μL of stock solution) were prepared in Tris buffer to a final volume of 3000 μL. Aliquots (10 or 20 μL) of titrant were added by pipette to a cuvette containing ligand (18 μL of stock solution) and Tris buffer (2982 μL). The absorbance at 320 nm was monitored until spectral changes ceased, at which point [Ba$^{2+}$]=[L]. From the volume of titrant added, the concentration of the stock solution of macroquin-SO$_3$ was calculated to be 8.17 mM, which was within 9% of the theoretical value of 8.96 mM based on mass.

Three independent solutions of each complex were prepared containing ligand (276.29-277.20 μM, 1.1 equiv) and Ba$^{2+}$ (1.0 equiv, from 1001 μg/mL ICP standard) in Tris buffer. Three independent positive control solutions were prepared in the same manner, except an aliquot of water was used in place of ligand. HAP challenges were initiated by adding an aliquot (20 μL) of the complex or control solution to a suspension of HAP (50±1 mg) in Tris (1980 μL). The final concentrations of ligand and Ba$^{2+}$ were 2.8 μM and 2.5 μM, respectively. The quantity of suspended HAP corresponds to a 20,000-fold molar excess compared to the concentration of Ba-L complex. The suspensions were stirred at room temperature (22±1° C.) using identical stir bars (10×3 mm) and a stir rate of 550 ppm. A piece of cardboard was placed beneath each vial to minimize the transfer of heat from the stir plate. At time points of 10 min, 1 h, 5 h, and 20 h, each suspension was allowed to settle for approximately 1 min. An aliquot (~1 mL) was removed and immediately centrifuged for 5 min (25° C., 15,000 RPM), and then a portion of supernatant was carefully transferred into a separate tube and analyzed as described below. Challenges were carried out in triplicate for each time point, except for the 5 h HAP challenge for Ba-macropa, which was performed in duplicate.

The supernatants were diluted 4-fold with water and analyzed for barium content by GFAAS using THGA graphite tubes with end caps, a wavelength of 553.6 nm, and a slit width of 0.2 nm. With the lamp used in this study, the lamp energy was typically 73 and the lamp current was set to 25 mA. Signals were processed in the background-corrected peak area mode. Autosampler cups were made of polypropylene. Significant ligand-dependent matrix effects were observed during method development. Therefore, for each Ba-L complex studied, calibration standards containing both ligand (2.8 μM) and barium (2.5 μM) were prepared in Tris buffer to match the conditions of the challenges. Each standard was diluted 4-fold with water to give a solution containing ~0.7 μM of ligand and ~0.625 μM (86 μg/L) of barium, which was used to construct the ligand-specific calibration curve. All calibrations consisted of 4 concentrations (21.5-86 μg/L) and were linear through zero (correlation coefficient>0.995). Water was employed as the diluent. The furance method is provided in the table below:

| Parameters | Temperature (° C.) | Ramp (s) | Hold (s) | Ar gas flow (mL/min) |
|---|---|---|---|---|
| Dry | 110 | 1 | 30 | 250 |
| Dry | 130 | 15 | 30 | 250 |
| Pyrolize | 1200 | 10 | 20 | 250 |
| Atomize | 2550 | 0 | 10 | 0 |
| Clean | 2600 | 1 | 15 | 250 |

Each sample was analyzed in triplicate and averaged. Between each sample, a single measurement of water was made to prevent barium carryover into the next sample measurement. After every 5 samples were analyzed, an independently prepared Ba-L calibration standard (86 µg/L of Ba) was analyzed a maximum of 2 times as a quality control check. If the second measurement was not within ±10% of the known concentration of barium the instrument was re-calibrated and the data between the failed calibration check and the previous calibration check was excluded. Data from each time point were averaged and the results are reported as the percentage of barium remaining in the liquid phase, reflecting intact Ba-L complex. The errors provided correspond to 1 standard deviation.

Barium Sulfate Dissolution Studies
Dissolution of Barium Sulfate

The encouraging results of the thermodynamic and kinetic stability studies prompted us to evaluate the feasibility of employing macropa and macropaquin as $BaSO_4$ scale dissolvers. First, a suspension of $BaSO_4$ in pH 8 $NaHCO_3$ was formed by combining $Ba(NO_3)_2$ (4.53 mM) with excess $Na_2SO_4$ (13.48 mM), simulating the mixing of incompatible waters that produces $BaSO_4$ scale in petroleum operations. The resulting $BaSO_4$ suspension was treated with ligand (5 mM), and the amount of dissolved $Ba^{2+}$ was measured by GFAAS.

Figures 5A, 5B:
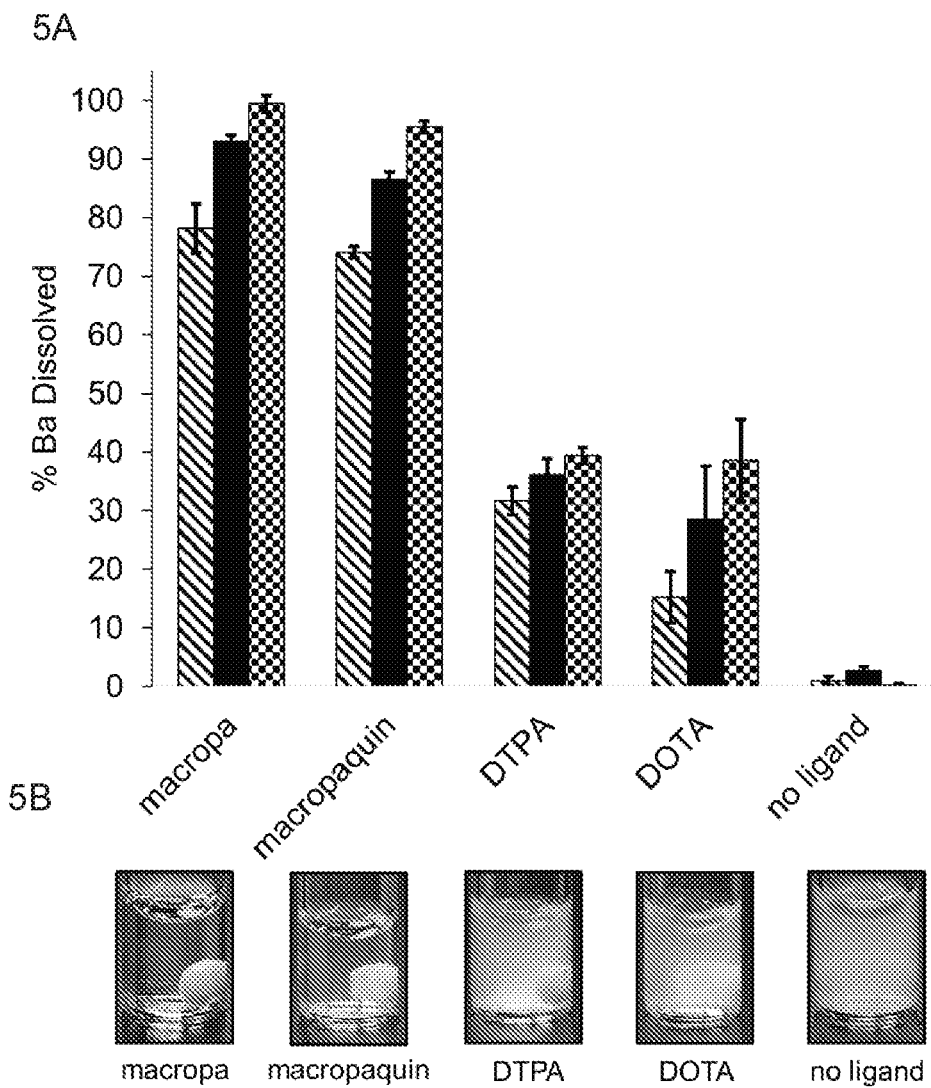
FIGS. 5A and 5B show the results of dissolution of $BaSO_4$ by macropa, macropaquin, DTPA, and DOTA.

FIGS. 5A and 5B show the results of dissolution of $BaSO_4$ by macropa, macropaquin, DTPA, and DOTA. FIG. 5A graphically presents the results of dissolution of $BaSO_4$ at RT and pH 8, as initiated by the addition of chelator (5 mM) to a suspension of $BaSO_4$ (4.53 mM $Ba(NO_3)_2$ and 13.48 mM $Na_2SO_4$). Barium content in solution was measured by GFAAS after 10, 20, and 30 min. FIG. 5B are photos of samples from dissolution experiments of $BaSO_4$ after 30 minutes for various chelating ligands (macropa, macropaquin, DTPA, DOTA, and no ligand). Macropa rapidly solubilized 78% of $BaSO_4$ in just 10 minutes and afforded complete dissolution after 30 minutes. Likewise, macropaquin dissolved 95% of $BaSO_4$ in 30 minutes. By contrast, the conventional ligands DOTA and DTPA dissolved only 40% of $BaSO_4$ within this same time, underscoring the inferior solubilizing properties of these ligands at pH 8.

The dissolution of $BaSO_4$ by macropa, DTPA, and DOTA was further evaluated in pH 11 $NaCO_3$ buffer to match the caustic conditions that are applied in the industrial setting. Impressively, macropa solubilized >95% of the $BaSO_4$ in just 5 min. DTPA also dissolved nearly all the $BaSO_4$ in this same time. The improved dissolution ability of DTPA at pH 11 versus pH 8 reflects the greater proportion of the fully deprotonated ligand ($DTPA^{5-}$) present at pH 11, which favors Ba-DTPA complex formation. These results are consistent with the fact that the petroleum industry only uses this ligand under conditions of high pH. The similar rates at which macropa and DTPA solubilize $BaSO_4$ at pH 11 suggest that macropa possesses remarkably fast $Ba^{2+}$-binding kinetics. The macrocycle DOTA, by contrast, was unable to completely dissolve all the $BaSO_4$. After 30 min, only 75% dissolution was reached, signifying that the kinetics of metal incorporation for DOTA remain slow even at high pH.

More specifically. $BaSO_4$ dissolution experiments at pH 8 were performed in $NaHCO_3$ (1 M, pH=7.9-8.0); dissolution studies at pH 11 were performed in $Na_2CO_3$ (1 M, pH adjusted to 10.98 using concentrated HCl). Stock solutions of macropa (19.34 mM for pH 8 studies and 21.84 mM for pH 11 studies), macropaquin (19.00 mM), DTPA (21.04 mM for pH 8 studies and 18.37 mM for pH 11 studies), and DOTA (19.94 mM) were all prepared in water. The concentrations of the macropa, macropaquin, and DTPA stocks were determined by quantitative NMR (n=2 for each ligand) using two independently prepared standards of potassium hydrogen phthalate in $D_2O$. The concentration of the DOTA stock solution was calculated from the mass of the ligand used (255.5 mg). A solution of $Na_2SO_4$ (293 mM) was prepared in water. The barium source for this experiment was an ICP standard solution of $Ba(NO_3)_2$ (72.99 mM; 10023 µg/mL) in 2% v/v $HNO_3$.

Dissolution studies were carried out in 2 mL borosilicate vials equipped with identical magnetic stir bars (6.4×3 mm). Each $BaSO_4$ suspension was prepared independently by mixing $Ba(NO_3)_2$ and $Na_2SO_4$ in 1 M $NaHCO_3$ or $Na_2CO_3$ to give final concentrations of 4.53 mM (621,426 µg/L) and 13.48 mM, respectively. Dissolution was initiated by the addition of an aliquot of ligand (5 mM final concentration, 1.1 equiv with respect to $Ba^{2+}$) to each suspension. Controls (pH 8) received an aliquot of water instead of ligand. The suspensions were stirred at room temperature (22±1° C.) at a rate of 550 RPM. At time points of 5 min (pH 11 only), 10 min, 20 min, and 30 min, the suspensions were filtered through nylon syringe filters (either 0.2 µm or 0.22 µm), and the filtrates were analyzed as described below. The dissolution experiments were performed in triplicate at every time point for each ligand except DOTA, for which 6 replicates were run for 20 min and 30 min time points at pH 8.

The filtered samples were diluted 6565-fold (65×101) with water and analyzed for barium content by GFAAS using the furnace method and instrument parameters discussed earlier above. Standards containing both ligand and barium at the same concentrations employed in the dissolution studies were prepared in either $NaHCO_3$ (pH 8) or $Na_2CO_3$ (pH 11); water was substituted for $Na_2SO_4$. Each standard was diluted 6565-fold with water to result in a solution containing 762 nM of ligand and 690 nM (95 µg/L) of barium, which was used to construct the ligand-specific calibration curve. All calibrations consisted of four concentrations (23.8-95 µg/L) and were linear through zero (correlation coefficient>0.995). Water was used as the diluent. Following calibration, each sample was analyzed in triplicate and averaged. After the analysis of every three samples, a single measurement of water was made to ensure that there was no carryover of barium. After every three (pH 11) or six (pH 8) samples were analyzed, an independently-prepared Ba-L standard was analyzed a maximum of two times as a quality control check. If the measurement was not within ±10% of the known concentration of barium, the instrument was re-calibrated and the data between the failed calibration check and the previous calibration check was excluded. Data from each time point were averaged and the results are reported as the percentage of barium dissolved. The errors given correspond to 1 standard deviation.

Dissolution of Barite Ore

Figures 6A, 6B, 6C, 6D:
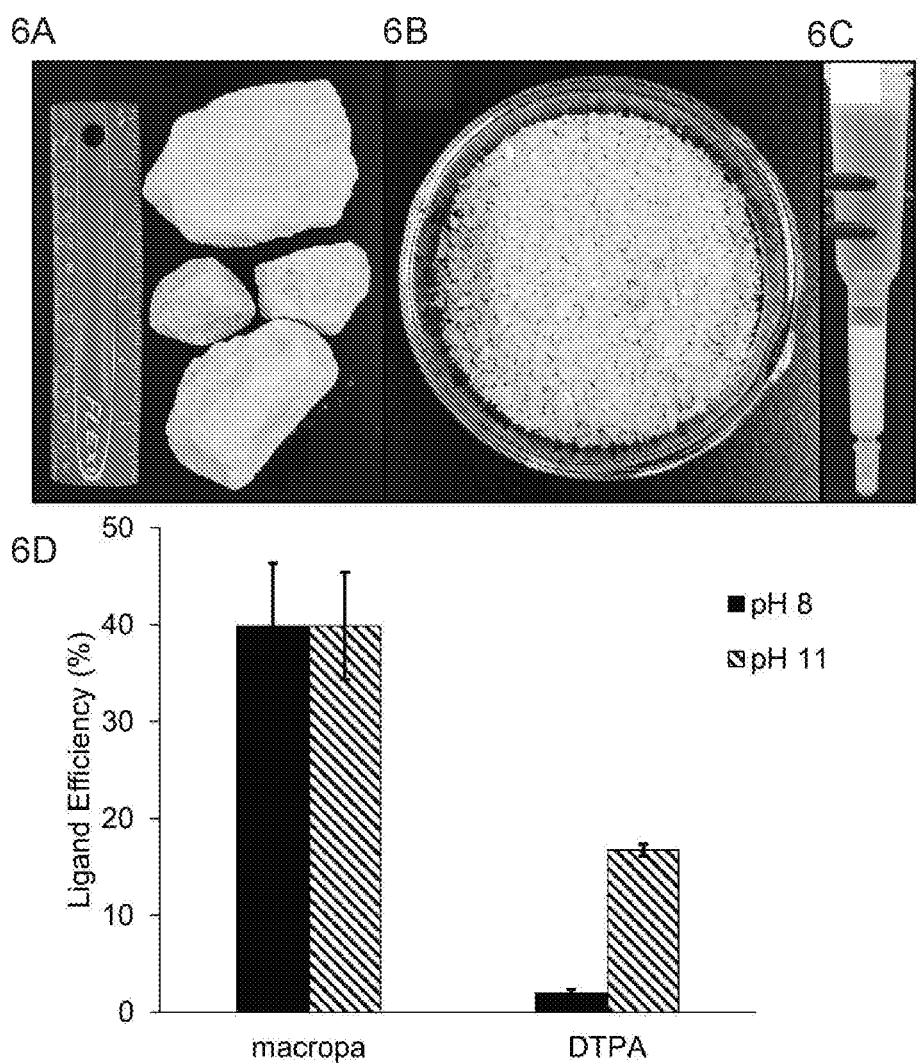
FIGS. 6A-6D show barite dissolution efficiency of macropa and DTPA.

The ligand-promoted dissolution of crude barite ore was next investigated. The crude barite ore is composed predominately of $BaSO_4$, as a model for the solid deposits of natural scale that plague the petroleum industry. Barite rocks (as shown in FIG. 6A) were milled and sieved to isolate particles between 0.5 and 2 mm (as shown in FIG. 6B). More specifically, a sample of barite crude ore was used. The rocks (approximately 1-3 inch pieces) were crushed using a hammer, and barite particles between 0.5 and 2 mm were isolated using a set of sieves. The barite was washed with deionized water and absolute ethanol to remove the fines, dried in an oven at 110° C., and then cooled in a dessicator.

To simulate production tubing clogged with $BaSO_4$ scale, polypropylene columns were filled with barite (3 g), to which solutions of macropa or DTPA at pH 8 or 11 were added (as shown in FIG. 6C). The concentration of each ligand solution was approximately 48 mM, consistent with the dilute compositions of scale dissolvers used industrially. After a soak time of 1 hour, the ligand solution was eluted from the column, and the concentration of dissolved barium was measured by GFAAS and converted to ligand efficiency, according to the following equation (eq. 5):

$$\text{Ligand Efficiency} = \frac{Ba_{exp}}{Ba_{max}} \times 100 \quad (5)$$

In Eq. 5 above, $Ba_{exp}$ is the concentration of barium measured in the eluate, and $Ba_{max}$ is the maximum concentration of barium that can be chelated by each ligand, calculated from the concentration of each ligand applied to the column and assuming a 1:1 M:L binding model. As shown in FIG. 6D, the ligand efficiency of macropa at pH 8 is 40%, indicating that nearly half of the ligand solution was saturated with $Ba^{2+}$ following exposure to barite for 1 hour. DTPA, by contrast, was practically incapable of dissolving barite at this pH, giving rise to a ligand efficiency of only 2%. Macropa remained equally as effective at pH 11, again displaying a ligand efficiency of 40%. By contrast, even at pH 11, the dissolution efficiency of DTPA was only 17%, less than half that observed for macropa. Collectively, these results indicate that macropa maximally dissolves barite at or below pH 8, underscoring its superior affinity for $Ba^{2+}$ near neutral pH.

Barite dissolution studies were conducted at pH 8 and pH 11. Ligands were dissolved in water and the pH of these solutions was adjusted with 2 M NaOH. The ligand concentrations (45.68-48.84 mM) were determined by quantitative NMR (n=2 for each ligand) using two independently prepared standards of potassium hydrogen phthalate in $D_2O$. Control solutions were prepared by adjusting the pH of 48 mM aqueous NaCl to either pH 8 or pH 11 using dilute NaOH and HCl. To simulate a pipeline clogged with $BaSO_4$ scale, polypropylene columns (chromatography columns, 2 mL bed volume) were filled with barite (3.00 g±0.01 g). Ligand or control solution (1 mL) was loaded onto each column by removing the column endcap until the liquid reached the bed support. After a soak time of 1 hour, the solution was eluted using a small positive pressure of air and filtered through a 0.22 μm nylon syringe filter. The filtrate was diluted 2,020-51,005-fold with water and analyzed for barium content by GFAAS using the method described below. The barite dissolution experiments were performed in triplicate for both ligands at each pH.

Calibration solutions containing both ligand (48-49 mM) and barium (48 mM) were prepared to a final volume of 2 mL using an ICP standard solution of barium (72.99 mM; 10023 μg/mL), pH 8 ligand solution (161.38 mM macropa, 157.05 mM DTPA), and water. The calibration solution for the controls was prepared in a similar manner, except pH 8 NaCl solution (150.4 mM) was used instead of ligand solution. Each standard was diluted 101×101×5-fold with water to result in a solution containing 0.94 μM (129.2 μg/L) of barium, which was used to construct the ligand-specific calibration curve. All calibrations consisted of four concentrations (32.3-129.2 μg/L) and were linear through zero (correlation coefficient>0.995). Water was employed as the diluent.

The furnace method is provided in the table below:

| Parameters | Temperature (° C.) | Ramp (s) | Hold (s) | Ar gas flow (mL/min) |
|---|---|---|---|---|
| Dry | 110 | 1 | 20 | 250 |
| Dry | 140 | 10 | 5 | 250 |
| Pyrolize | 700 | 10 | 20 | 250 |
| Atomize | 2300 | 0 | 8 | 0 |
| Clean | 2500 | 1 | 10 | 250 |

Each sample was analyzed in triplicate and averaged. Between each sample, a single measurement of water was made to prevent barium carryover into the next sample measurement. After every three samples were analyzed, an independently prepared Ba-L calibration standard (129.2 μg/L of Ba) was analyzed a maximum of two times as a quality control check. If the second measurement was not within ±10% of the known concentration of barium, the instrument was re-calibrated and the data between the failed calibration check and the previous calibration check was excluded. Data for each set of triplicate samples were averaged and the results are reported in terms of ligand efficiency (%):

$$\text{Ligand Efficiency} = \frac{Ba_{exp}}{Ba_{max}} \times 100 \quad (6)$$

In the above equation, $Ba_{exp}$ is the concentration of barium (μg/L) measured in the liquid eluted from the column and $Ba_{max}$ is the maximum concentration of barium (μg/L) that can be chelated by each ligand upon dissolution of $BaSO_4$, calculated from the exact concentration of each ligand solution used and assuming a 1:1 M:L binding model. For example, macropa at a concentration of 48.84 mM can dissolve a maximum amount of 48.84 mM $BaSO_4$, equaling 6,707,197 μg/L barium. If a concentration of 3,353,598 μg/L of barium is measured in the eluted sample by GFAAS, the ligand efficiency is 50%, indicating that 50% of the ligand solution completed barium. The errors provided correspond to 1 standard deviation. No barium was detected in the control experiments at pH 8 and pH 11.

Recovery and Reuse of Macropa

Figure 7:
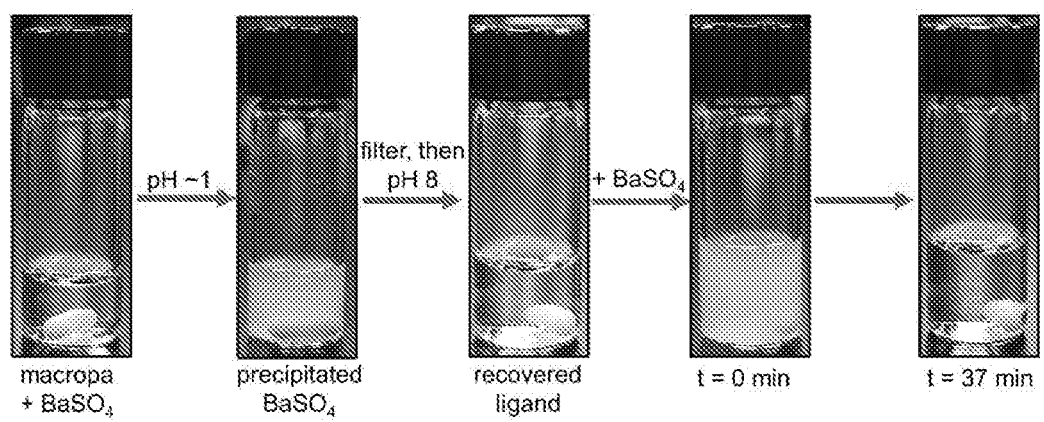
FIG. 7 schematically depicts, with photographs, a process for ligand recovery and reuse. A solution of macropa-dissolved $BaSO_4$ was acidified to release the $Ba^{2+}$ from the ligand as $BaSO_4$. After filtration of the precipitated $BaSO_4$ and basification of the solution, the recovered ligand was successfully reused for another cycle of $BaSO_4$ dissolution.

The capacity for recovery and reuse of macropa post-$BaSO_4$ dissolution was assessed qualitatively. FIG. 7 schematically depicts a process for ligand recovery and reuse. A solution of macropa-dissolved $BaSO_4$ was acidified to release the $Ba^{2+}$ from the ligand as $BaSO_4$. After filtration of the precipitated $BaSO_4$ and basification of the solution, the recovered ligand was successfully reused for another cycle of $BaSO_4$ dissolution. More specifically, a sample of macropa-dissolved $BaSO_4$ (9.66 mM macropa, 8.74 mM $Ba(NO_3)_2$, 26.04 mM $Na_2SO_4$) was acidified to pH 1 with concentrated HCl to protonate the ligand, inducing $Ba^{2+}$ decomplexation and precipitation as $BaSO_4$. The macropa solution was isolated by filtration, basified to pH 8 with 2 M NaOH, and combined with another portion of $BaSO_4$. Within 40 minutes, no visible precipitate remained in the vial, signaling that the recycled macropa dissolved all the $BaSO_4$. Subsequently, the ligand was recovered and reused for $BaSO_4$ dissolution four more times with a negligible loss in efficacy or speed of dissolution. These results demonstrate the facile and economic reuse of macropa, an attractive feature that will facilitate its implementation in industry.

In other experiments, an initial solution of macropa-dissolved $BaSO_4$ was prepared by stirring at 450 RPM a suspension containing $BaSO_4$ (8.74 mM $Ba(NO_3)_2$; 26.04 mM Na$_2$SO$_4$), macropa (9.66 mM), and 2M NaOH (35 μL) in 1M NaHCO$_3$ (326 μL). The final volume was 1035 μL and the pH was 8. After 17 minutes, a clear and colorless solution was observed, reflecting the complete dissolution of BaSO$_4$. The solution was adjusted to pH 1 (by litmus paper) by adding concentrated HCl (3 drops). The resultant suspension was stirred for 10 minutes and then filtered through a nylon syringe filter (0.22 μm). The syringe filter was rinsed with 0.1 M HCl (2×100 μL) to facilitate full recovery of the ligand. The pH of the filtrate was carefully adjusted back to pH 8 (by litmus paper) with 2 M NaOH. To this recovered solution of macropa was added another portion of BaSO$_4$ (0.009 mmol BaNO$_3$, 0.027 mmol Na$_2$SO$_4$). The suspension was stirred at 450 RPM and RT. The dissolution of BaSO$_4$ was monitored visually until all of the BaSO$_4$ was dissolved, marking the completion of a full cycle of ligand recovery and reuse. Another cycle was then initiated via the addition of concentrated HCl to the solution. A total of five cycles were performed and the time to full dissolution of BaSO$_4$ was recorded. Despite the marginal amount of precipitate that persisted after an extended period of stirring during the 4th and 5th cycles, dissolution of most of the BaSO$_4$ was rapidly achieved within the first hour. The precipitate may be attributed to a small amount of BaSO$_4$ that remains undissolved as a consequence of ligand loss over time, which occurs because aliquots of the solution are removed to assess the pH during the recovery and reuse process.

In summary, three ligands based on the expanded diaza-18-crown-6 macrocycle were evaluated for their abilities to chelate the large Ba$^{2+}$ ion. Macropa exhibits unprecedented affinity for Ba$^{2+}$ at pH 7.4, possessing a log K' value of 10.74. The Ba$^{2+}$ complexes of both macropa and macropaquin display substantial kinetic stability when challenged with La$^{3+}$ or HAP, whereas macroquin-SO$_3$ rapidly releases Ba$^{2+}$ under these conditions. Additionally, macropa and macropaquin can efficiently dissolve BaSO$_4$ under RT and near-neutral pH conditions. This feature was further reflected in dissolution studies involving authentic barite ore samples, which showed macropa to be superior to the state-of-the-art chelator DTPA. The unexpectedly efficient Ba$^{2+}$-chelation properties of the ligands described herein renders them useful for the dissolution of BaSO$_4$ scale deposits, fulfilling an important need in the petroleum industry.

While there have been shown and described what are at present considered the preferred embodiments of the invention, those skilled in the art may make various changes and modifications which remain within the scope of the invention defined by the appended claims.

What is claimed is:

1. A metal-chelating composition having the following structure:

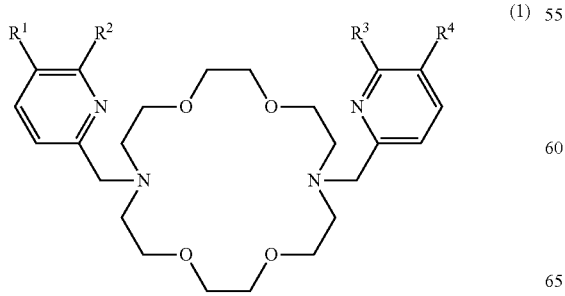

(1)

wherein:
R$^1$, R$^2$, R$^3$, and R$^4$ are independently selected from the following groups: (i) hydrogen atom, (ii) hydrocarbon groups (R) containing 1-12 carbon atoms; (iii) halogen atoms; (iv) —P(R$^5$)(=O)OH groups; (v) —C(=O)OH groups; (vi) —S(=O)$_2$OH groups; and (vii) —OH groups, wherein R$^5$ is selected from hydrocarbon groups (R) and —OH;

R$^1$ and R$^2$ may optionally interconnect to form Ring A fused to the ring on which R$^1$ and R$^2$ are present;

R$^3$ and R$^4$ may optionally interconnect to form Ring B fused to the ring on which R$^3$ and R$^4$ are present;

wherein Ring A and Ring B are optionally and independently substituted with one or more of groups (ii)-(vii);

wherein
at least one of R$^2$ and R$^3$ is (iv) —P(R$^5$)(=O)OH; or
at least one of Ring A and Ring B is present and is substituted with (iv) —P(R$^5$)(=O)OH or (vii) —OH; or
only one of Ring A and Ring B is present and is substituted with at least one group selected from (iv) —P(R$^5$)(=O)OH, (vi) —S(=O)$_2$OH, or (vii) —OH.

2. The composition of claim 1, wherein at least one of R$^2$ and R$^3$ is (iv) —P(R$^5$)(=O)OH, or at least one of Ring A and Ring B is present and is substituted with (iv) —P(R$^5$)(=O) OH.

3. The composition of claim 1, wherein R$^2$ and R$^3$ are both (iv) —P(R$^5$)(=O)OH.

4. The composition of claim 1, wherein the composition has a structure according to Formula (1a) or Formula (1b):

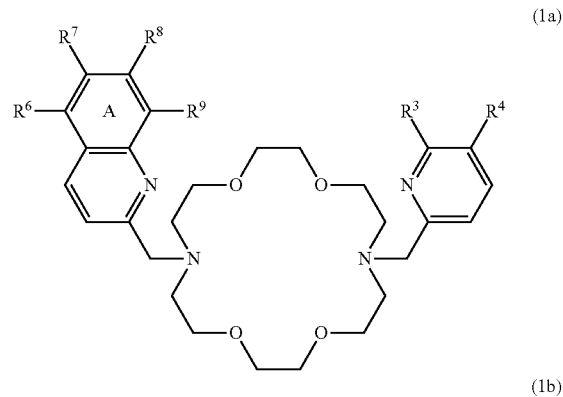

(1a)

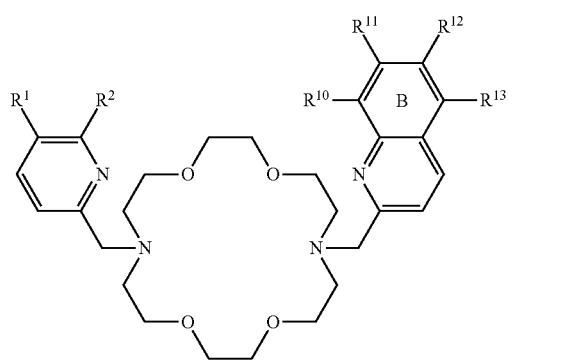

(1b)

wherein:
R$^6$, R$^7$, R$^8$, R$^9$, R$^{10}$, R$^{11}$, R$^{12}$, and R$^{13}$ are independently selected from the following groups: (i) hydrogen, (ii) a hydrocarbon group (R) containing 1-12 carbon atoms; (iii) a halogen; (iv) —P(R⁵)(=O)OH; (v) —C(=O)OH; (vi) —S(=O)₂OH; and (vii) —OH, wherein R⁵ is selected from a hydrocarbon group (R) and —OH;

provided that

R³ is (v) —C(=O)OH, and at least one of R⁶, R⁷, R⁸ and R⁹ is (vii) —OH; or

R³ is (vii) —OH, and at least one of R⁶, R⁷, R⁸ and R⁹ is (v) —C(=O)OH; or

R² is (v) —C(=O)OH, and at least one of R¹⁰, R¹¹, R¹², and R¹³ is (vii) —OH; or

R² is (vii) —OH, and at least one of R¹⁰, R¹¹, R¹², and R¹³ is (v) —C(=O)OH.

5. A method of chelating a metal ion having an atomic number of at least 56, the method comprising contacting a salt of said metal ion with a metal-chelating composition while both the salt and metal-chelating composition are in contact with an aqueous-based liquid, the metal-chelating composition having the following structure:

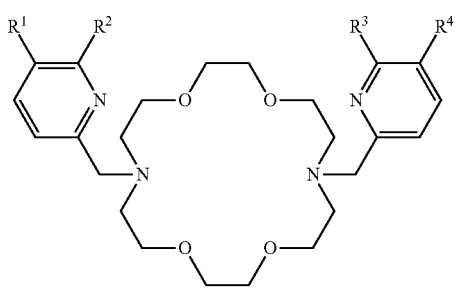

(1)

wherein:

R¹, R², R³, and R⁴ are independently selected from the following groups: (i) hydrogen atom, (ii) hydrocarbon groups (R) containing 1-12 carbon atoms; (iii) halogen atoms; (iv) —P(R⁵)(=O)OH groups; (v) —C(=O)OH groups; (vi) —S(=O)₂OH groups; and (vii) —OH groups, wherein R⁵ is selected from hydrocarbon groups (R) and —OH;

R¹ and R² may optionally interconnect to form Ring A fused to the ring on which R¹ and R² are present;

R³ and R⁴ may optionally interconnect to form Ring B fused to the ring on which R³ and R⁴ are present;

wherein Ring A and Ring B are optionally and independently substituted with one or more of groups (ii)-(vii);

wherein at least one of R² and R³ is (iv) —P(R⁵)(=O)OH; or at least one of Ring A and Ring B is present and is substituted with (iv) —P(R⁵)(=O)OH or (vii) —OH; or only one of Ring A and Ring B is present and is substituted with at least one group selected from (iv) —P(R⁵(=O)OH, (vi) —S(=O)₂OH, or (vii) —OH.

6. The method of claim 5, wherein the chelating composition has the following structure:

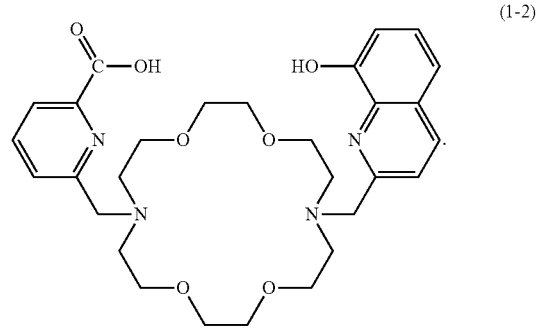 [SMILES: O=C(O)c1cccc(CN2CCOCCOCCN(Cc3ccc4cccc(O)c4n3)CCOCCOCC2)n1]

(1-2)

7. The method of claim 5, wherein at least one of Ring A and Ring B is present and is substituted with (vii) —OH.

8. The method of claim 7, wherein the chelating composition has the following structure:

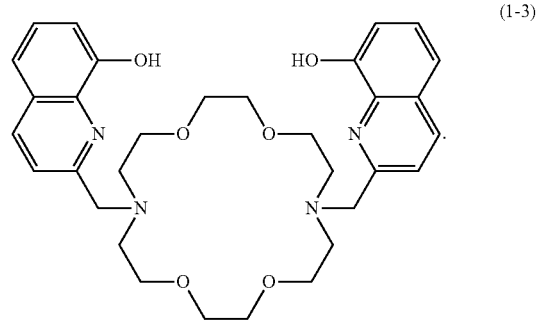 [SMILES: Oc1cccc2ccc(CN3CCOCCOCCN(Cc4ccc5cccc(O)c5n4)CCOCCOCC3)nc12]

(1-3)

9. The method of claim 5, wherein at least one of R² and R³ is (iv) —P(R⁵)(=O)OH, or at least one of Ring A and Ring B is present and is substituted with (iv) —P(R⁵)(=O)OH.

10. The method of claim 9, wherein the chelating composition has the following structure:

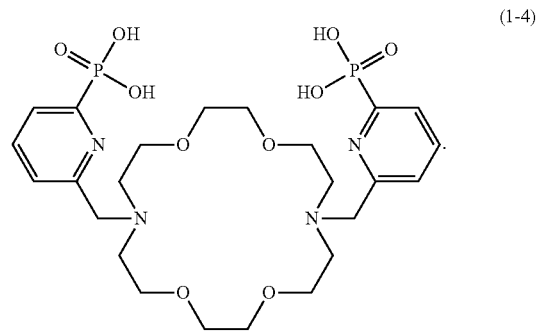 [SMILES: O=P(O)(O)c1cccc(CN2CCOCCOCCN(Cc3cccc(P(=O)(O)O)n3)CCOCCOCC2)n1]

(1-4)

11. The method of claim 5, wherein said metal ion having an atomic number of at least 56 comprises barium.

12. The method of claim 11, wherein the barium is within a barium scale deposit and the method results in dissolution of the barium from the barium scale deposit into the aqueous-based liquid to result in at least partial removal of the barium scale deposit.

13. The method of claim 12, wherein said dissolution is achieved while the aqueous-based liquid is at a temperature of no more than 30° C. and has a pH of 5-10.

14. The method of claim 12, wherein said dissolution is achieved while the aqueous-based liquid is at a temperature of no more than 30° C. and has a pH of 5-8.

15. The method of claim 11, wherein the metal-chelating composition selectively chelates barium over the lighter alkaline earth elements.

16. The method of claim 11, wherein said metal ion having an atomic number of at least 56 further comprises radium.

17. The method of claim 16, wherein the radium is within a barium scale deposit, and the method results in dissolution of the barium and radium from the barium scale deposit into the aqueous-based liquid to result in at least partial removal of the barium scale deposit.

18. The method of claim 11, wherein the metal-chelating composition selectively chelates barium and radium over the lighter alkaline earth elements.

19. The method of claim 5, wherein a barium-containing aqueous liquid is in contact with a conduit for transporting and/or processing of said barium-containing aqueous liquid, and the metal-chelating composition is dissolved in said barium-containing aqueous liquid to inhibit formation or growth of a barium scale deposit on said conduit.

* * * * *